US007189519B2

(12) United States Patent
Sklar et al.

(10) Patent No.: US 7,189,519 B2
(45) Date of Patent: Mar. 13, 2007

(54) BEAD-BASED DETECTION OF LIGAND-GPCR-G PROTEIN COMPLEXES

(75) Inventors: Larry A. Sklar, Albuquerque, NM (US); Tione Buranda, Albuquerque, NM (US); Daniel Cimino, Tijeras, NM (US); Alex T. Key, Albuquerque, NM (US); Richard Neubig, Scio, MI (US); Peter C. Simons, Albuquerque, NM (US); Eric R. Prossnitz, Albuquerque, NM (US); Mei Shi, Albuquerque, NM (US)

(73) Assignees: STC.UNM, Albuquerque, NM (US); Univeristy of Michigan, Ann Arbor, MI (US)

( * ) Notice: Subject to any disclaimer, the term of this patent is extended or adjusted under 35 U.S.C. 154(b) by 383 days.

(21) Appl. No.: 10/429,042

(22) Filed: May 5, 2003

(65) Prior Publication Data

US 2003/0235863 A1 Dec. 25, 2003

Related U.S. Application Data

(63) Continuation-in-part of application No. 09/370,358, filed on Aug. 9, 1999.

(60) Provisional application No. 60/378,536, filed on May 6, 2002, provisional application No. 60/096,010, filed on Aug. 10, 1998.

(51) Int. Cl.
*G01N 33/52* (2006.01)
*G01N 33/566* (2006.01)
*C12N 1/20* (2006.01)
*C07K 1/00* (2006.01)
*C07H 21/04* (2006.01)

(52) U.S. Cl. .................. 435/7.1; 436/501; 436/56; 436/172; 435/252.3; 530/350; 530/402; 536/23.5; 536/24.2

(58) Field of Classification Search ............... None
See application file for complete search history.

(56) References Cited

U.S. PATENT DOCUMENTS

| 4,275,149 A | 6/1981 | Litman et al. |
| 4,665,020 A | 5/1987 | Saunders |
| 5,405,784 A | 4/1995 | VanHoegaerden |
| 5,583,010 A | 12/1996 | Baumbach et al. |
| 5,601,992 A | 2/1997 | Lemer et al. |
| 5,639,603 A | 6/1997 | Dower |
| 5,698,685 A | 12/1997 | Summerton et al. |
| 5,747,349 A | 5/1998 | Van den Engh et al. |
| 5,763,585 A | 6/1998 | Nag |
| 6,448,377 B1 | 9/2002 | Kobilka et al. |

OTHER PUBLICATIONS

Kozasa T. 2004. Methods in Molecular Biology. 237:21.*
Eppler CM et al., 1992. J Biol Chem. 267:15603.*
Sklar LA. 2000. Biotechniques 28:976-985.*
Bendar, B., et al., "Flow cytometric measurement of kinetic and equilibrium binding parameters of argine-glycine-asparatic acid ligands binding to glycoprotein IIb/IIa on platelets." *Cytometry.* Feb. 1997, vol. 28, pp. 58-65.
David, N. E., et al. "Expression and purification of the *Saccharamyces cerevisiae* alpha-factor receptor (Ste2p), a 7-transmembrane-segment G protein-coupled receptor." *J. Biol. Chem.* Jun. 1997, vol. 272, No. 24, pp. 15553-15561.
Eppler et al., J. Biol. Chem 267:22(15603-15612)92.
Jayawickreme et al., PNAS 91(1614-1618)1994.
Jones et al., J. Chromatography A 707(3-22)1995.
Lindner, P., et al., "Specific detection of His-tagged proteins with recombinant anti-his tag scFv-phosphatase or scFv-phage fusions." *BioTechniques.* Jan. 1997, vol. 22, No. 1, pp. 140-149, especially p. 142.
Robeva et al., Biochem. Pharm. 51:545-555, 1996.
Robeva, A. S. et al., "Double tagging recombinant A1 and A2a adenosine receptors with hexahistidine and the FLAG epitope." *Bioch. Pharm.* Jan. 1996, vol. 51, pp. 545-555.
Robeva, AS et al., Drug Development Research 39(243-252)1996.
Sklar, Larry A., et al., "Regulation of Ligand-Receptor Dynamics by Guanine Nucleotides", Journal of Biological Chemistry, vol. 262, No. 1, pp. 135-139, Jan. 5, 1987.
Wang, Ning and Donald E. Jngber, "Probing Transmembrane Mechanical Coupling and Cytomechanics Using Magnetic Twisting Cytometry," Biochem. Cell Bio. vol. 73, pp. 327-335 1995.
Buranda et al., "Peptides, Antibodies, and FRET on Beads in Flow Cytometry", *Cytometry* (1999) 37:21-31.
Wenzel-Seifert et al., "Quantitative Analysis of Formyl Peptide Receptor Coupling", *J. Biol. Chem.* (1999) 274:33259-32266.
Zuck et al., "Ligand-receptor Binding Measured by Laser-scanning Imaging" *Proc. Natl. Acad. Sci. USA* (1999) 96:11122-11127.
Sklar et al., "Solubilization and Display of G Protein-Coupled Receptors on Beads for Real-Time Fluorescence and Flow Cytometric Analysis" *BioTechniques* 28:976-985 (2000).

* cited by examiner

*Primary Examiner*—Lorraine Spector
*Assistant Examiner*—Shulamith H Shafer
(74) *Attorney, Agent, or Firm*—Henry D. Coleman; R. Neil Sudol; William J. Sapone

(57) ABSTRACT

The present invention provides a general approach for G protein coupled receptors that may be used to define agonists and antagonists, and the specificity of receptor coupling to G protein subunits. Methods of the present invention use small volumes (microliters) and are compatible with high throughput flow cytometry. When assays of the present invention are multiplexed, the specificity of the interactions of a receptor with many G proteins may be determined simultaneously.

11 Claims, 14 Drawing Sheets

Changes from the standard assembly:

1. No αβγ
2. No α
3. (standard)
4. +GTPγS
5. Irrelevant L-fl
6. No R

1. No βγ
2. +GTPγS
3. (standard)
4. 0.1 μM GTP
5. 0.5 μM GTP
6. 1 μM GTP
7. 5 μM GTP
8. 10 μM GTP
9. 25 μM GTP
10. 50 μM GTP
11. 200 μM GTP 1. No αβγ
2. No α
3. (standard)
4. +GTPγS
5. No L

BEAD-BASED DETECTION OF LIGAND-GPCR-G PROTEIN COMPLEXES

CROSS-REFERENCE TO RELATED APPLICATIONS

This continuation-in-part application makes reference to and claims priority to U.S. Provisional Patent Application No. 60/378,536, entitled "Drug Discovery Systems and Methods and Compounds for Drug Delivery," filed May 6, 2002, and U.S. patent application Ser. No. 09/370,358, entitled "Display of Receptors and Analysis of Binding Interactions and Drug Libraries," filed Aug. 9, 1999, which claims priority to U.S. Provisional Patent Application No. 60/096,010, entitled "Solid Phase Display of Combinatorial Libraries and Non-Cellular Display of 7 TMR," filed Aug. 10, 1998. The entire disclosures and contents of the above applications are hereby incorporated by reference.

GOVERNMENT INTEREST STATEMENT

This invention is made with government support under Grant Numbers GM60799/EB-00264, HL-46417, GM-39561 awarded by the National Institutes of Health and Grant Number MCB-9907611 awarded by the National Science Foundation. The government may have certain rights in this invention.

BACKGROUND OF THE INVENTION

1. Field of the Invention

The present invention relates generally to molecular assemblies, and more particularly to an assay for the detection of GPCR molecular assemblies and bead-based detection of ligand-GPCR complexes.

2. Description of the Prior Art

G protein coupled receptors (GPCRs) interact with extracellular stimuli, such as photons, hormones, neurotransmitters, and odorants, see Gilman A G (1995), Nobel Lecture, G Proteins and Regulation of Adenylyl Cyclase, Biosci Rep, 15, pp 65–97, the entire contents and disclosure of which is hereby incorporated by reference. These stimuli cause coformational changes in the receptor leading to binding of intracellular G protein heterotrimers, each with one copy of a guanyl nucleotide binding α subunit, and a βγ dimer, see Neer E J (1995), Heterotrimeric G Proteins: Organizers of Transmembrane Signals, Cell, 80, pp 249–257, the entire contents and disclosure of which is hereby incorporated by reference. After stimulation, the α subunit binds GTP, which promotes dissociation of the α subunit from the βγ dimer, exposing new surfaces to cytoplasmic effectors, such as adenylyl cyclase and phospholipase C. The human genome contains ~600 GPCR genes, 27 α, 5 β, and 13 γ, see Venter et al. (2001), The Sequence of the Human Genome, Science, 291, pp 1304–1351, the entire contents and disclosure of which is hereby incorporated by reference, with smaller numbers of these G proteins (17, 5 and 12, respectively) found to date. With such large numbers, determining how productively any given GPCR couples to a particular αβγ heterotrimer is daunting (1,020 αβγ combinations alone). The assembly of a high agonist-affinity complex is a good criterion of productive partners, see Gilman A G (1987), G Proteins: Transducers of Receptor-Generated Signals, Ann Rev Biochem, 56, pp 615–649, the entire contents and disclosure of which is hereby incorporated by reference.

The formyl peptide receptor (FPR) responds to the presence of N-formyl methionine-containing peptides resulting from bacterial and mitochondrial protein synthesis, as well as other hydrophobic peptides, see Gao et al. (1994), A High Potency Nonformylated Peptide Agonist for the Phagocyte N-Formylpeptide Chemotactic Receptor, J Exp Med, 180, pp 2191–2197, the entire contents and disclosure of which is hereby incorporated by reference. This receptor has served as a model for signal transduction in phagocytic cells and for inflammatory and autoimmune diseases, see Prossnitz E R and Ye R D (1997), The N-Formyl Peptide Receptor: a Model for the Study of Chemoattractant Receptor Structure and Function, Pharacol Ther, 74, pp 73–102, the entire contents and disclosure of which is hereby incorporated by reference. The receptor has been cloned and overexpressed in tissue culture cells, solubilized, and assembled with a formyl peptide ligand and G protein to form a high agonist-affinity ternary complex in solution, see Bennett et al. (2001), Real-Time Analysis of G Protein-Coupled Receptor Reconstitution in a Solubilized System, J Biol Chem, 276, pp 22453–22460, the entire contents and disclosure of which is hereby incorporated by reference.

The soluble receptor reconstitutes with ligand, G proteins, and arrestin in a manner that is sensitive to receptor phosphorylation and mutations in both the receptor and G proteins. The assembly may be measured in real-time with fluorescent ligands, and the assemblies are consistent with cellular co-localizations observed by fluorescence confocal microscopy, see Bennett et al. (2001), Real-Time Analysis of G Protein-Coupled Receptor Reconstitution in a Soubilized System, J Biol Chem, 276, pp 22453–22460; Bennett et al. (2001), Partial Phosphorylation of the N-Formyl Peptide Receptor Inhibits G Protein Association Independent of Arrestin Binding, J Biol Chem, 276, pp 49195–49203; and Key et al. (2001), Regulation of Formyl Peptide Receptor Agonist Affinity by Reconstitution with Arrestins and Heterotrimeric G Proteins, J Biol Chem, 276, pp 49204–49212, the entire contents and disclosures of which are hereby incorporated by reference.

While ternary complex assemblies have been the subject of experimental investigation and mathematical modeling over several decades, see Kent et al. (1980), A Quantitative Analysis of Beta-Adrenergic Receptor Interactions: Resolution of High and Low Affinity States of the Receptor by Computer Modeling of Ligand Binding Data, Mol Pharmacol, 17, pp 14–23, the entire contents and disclosure of which is hereby incorporated by reference, the tools to examine the affinities and kinetics of individual steps in complex formation, disassembly, activation, and termination have only been accessible in a limited way, see Christopoulos A and Kenakin T (2002), G Protein-Coupled Receptor Allosterism and Complexing, Pharmacol Rev, 54, pp 323–374, the entire contents and disclosure of which is hereby incorporated by reference. For rhodopsin, it has been possible to measure complex assembly and disassembly through the spectroscopic signature of the metarhodopsin II-transducin complex, see Mitchell et al. (2001), Optimization of Receptor-G Protein Coupling by Bilayer Lipid Composition I: Kinetics of Rhodopsin-Transducin Binding, J Biol Chem, 276, pp 42801–42806, the entire contents and disclosure of which is hereby incorporated by reference. GPCRs also activate transmembrane channels in the subsecond time frame, see Mark et al. (2000), G Protein Modulation of Recombinant P/Q-Type Calcium Channels by Regulators of G Protein Signaling Proteins, J Physiol, 528, Pt. 1, pp 65–77, the entire contents and disclosure of which is hereby incorporated by reference, where ternary complex dynamics can be inferred from measurements of ion currents. Such measurements have given a $G_t$ (transducin) activation rate of ~120 s$^{-1}$, see Leskov et al. (2000), The Gain of Rod Phototransduction: Reconciliation of Biochemical and Electrophysiological Measurements, Neuron, 27, pp 525–537, the entire contents and disclosure of which is hereby incorporated by reference, probably unique to the visual transduction system, and a G$_q$ (a heterotrimeric G protein in which the α subunit is the q subtype, α$_q$) activation rate of 2 s$^{-1}$, Muldiopadhyay S and Ross E M (1999), Rapid GTP Binding and Hydrolysis by G(q) Promoted by Receptor and GTPase-Activating Proteins, Proc Natl Acad Sci USA, 96, pp 9539–9544, the entire contents and disclosure of which is hereby incorporated by reference. Both surface plasmon resonance, see Rebois (2002), Elucidating Kinetic and Thermodynamic Constants for Interaction of G Protein Subunits and Receptors by Surface Plasmon Resonance Spectoscopy, Methods in Enzymology (Iyengar Ra and Hildebrandt J D, eds), Academic Press, New York, pp 15–42, the entire contents and disclosure of which is hereby incorporated by reference, and flow cytometry, see Nolan J P and Sklar L A (1998), The Emergence of Flow Cytometry for Sensitive, Real-Time Measurements of Molecular Interactions, Nat Biotechnol, 16, pp 633–638, the entire contents and disclosure of which is hereby incorporated by reference, could be general tools for measuring individual rate constants.

Therefore, appropriate tools in these areas have been limited and, in many situations, unsatisfactory. Thus, there is a need for a homogeneous, small volume bead-based approach compatible with high throughput flow cytometry, which would allow evaluation of G protein coupled receptor molecular assemblies.

SUMMARY OF THE INVENTION

It is therefore an object of the present invention to provide a homogeneous, small volume bead-based approach compatible with high throughput flow cytometry.

It is a further object to provide a small volume bead-based approach that provides for evaluation of G protein coupled receptor molecular assemblies.

It is a further object to provide a method for coating beads with functional G proteins, hereafter named G protein beads.

It is a further object to provide a method for detection of ligands, which uses a GPCR-GFP fusion protein in combination with G protein beads.

According to a first broad aspect of the present invention, there is provided a method comprising the steps of: providing a sample suspension containing at least one set of G protein beads, each of the G-protein beads comprising epitope-recognizing beads having a heterotrimeric G protein bound thereto; mixing the sample suspension with at least one type of G protein coupled receptor and a ligand to thereby form a mixed suspension containing a ligand-receptor-G protein complex when the G protein is capable of forming complex with the receptor and the ligand; and mixing the mixed suspension to incubate the mixed suspension and thereby form an incubated suspension; detecting the formation of a stable ligand-receptor-G protein complexes in the incubated suspension by flow cytometry.

According to second broad aspect of the invention, there is provided a method of forming G protein beads comprising the steps of: providing epitope-recognizing beads; and binding epitope-bearing G protein subunits to the epitope-recognizing beads to form G protein beads.

Other objects and features of the present invention will be apparent from the following detailed description of the preferred embodiment.

BRIEF DESCRIPTION OF THE DRAWINGS

The invention will be described in conjunction with the accompanying drawings, in which:

In FIG. 1A, fluorescent ligand (L$^F$) was incubated in the presence of an unknown amount of solubilized formyl peptide receptor in 200 μl aliquots in a spectrofluorimeter with stirring as described in the experimental procedures discussed herein. After obtaining an initial fluorescence, an antibody that quenched the fluorescence of free L$^F$ was added, and the resulting fluorescence was monitored over time. The dotted line, representing 2 nM L$^F$ added to a cuvet without receptor, has been shifted down for clarity. Two traces are shown for the addition of 2 nM L$^F$: the solid line shows the fluorescence for a solution containing receptor, while the dotted line shows the fluorescence for a solution without receptor (or with blocked receptor). The point at which the receptor-containing line with 2 nM L$^F$ departed from the receptor-free (or blocked receptor) dotted line measured the proportion of free ligand (above the point) and receptor-bound ligand (below the point). This pair of values defined the first square in FIG. 1B, at 0.7 nM L$^F$ bound, 1.3 nM L$^F$ free. In FIG. 1B, concentrations of free L$^F$ and receptor-bound L$^F$ were obtained for each beginning concentration of L$^F$. These paired values were plotted to obtain the dissociation constant of the L$^F$ for the receptor and the concentration of the receptor.

FIG. 2A is a dot plot of forward scatter vs. side scatter; FIG. B is a histogram of DCNi with 0 or 10 nM hexahistidine-tagged green fluorescent protein (H6-GFP); FIG. 2C is a time course of DCNi binding to 10 nM H6-GFP in the presence of 10 mM EDTA (inverted triangles), absence of EDTA (triangles), and with 10 mM EDTA added after 30 min (open squares); FIG. 2D shows DCNi binding to H6-GFP through five washes over two hours (triangles) and with 10 mM EDTA added after two hours (open squares), where beads were kept in suspension with moderate mixing at 0–4° C., and 200 μl aliquots were removed for flow cytometric measurement of bead fluorescence; FIG. 2E represents membranes from cells expressing N-terininal hexahistidine-tagged FPR (N-H6:FPR) or C-terminal hexahistidine-tagged FPR (FPR:C-H6) which were solubilized as described in the experimental procedures discussed herein, with 18.5 nM FPR:C-H6 or 10 nM N-H6:FPR, and incubated with 50,000 DCNi beads in 200 μl of 0.1% dodecyl maltoside in buffer A with moderate mixing for seven hours in duplicate, where the beads were washed by centrifugation and resuspended in fresh buffer, incubated with various concentrations of L$^F$ as shown in the graph for 30 min, and then the bead fluorescence was measured by flow cytometry; and FIG. 2F shows the dissociation of L$^F$ from beads, which were coated with FPR:C-H6 in FIG. 2E, which was monitored using a custom built rapid mixer, as described in the experimental procedures discussed herein. The initial bead fluorescence was measured for twenty seconds, then an anti-FITC antibody was mixed with the beads, and the decrease in bead fluorescence was measured for another 100 seconds. The line shown is a best fit to a plateau, followed by an exponential decrease to the bottom.

In FIG. 4A, a fluorescent ligand ($L^F$) was used with wild type formyl peptide receptor (R) to detect the assembly of $L^F$RG on DCNi beads. Previous work with LRG complexes in solution had shown that ternary complex formation was complete in two hours at 4° C. in a 10 µl LRG assembly assay starting with concentrations of $L^F$=20 nM, and of R and G of about 100 nM. The 10 µl assay was then diluted to 200 µl for spectrofluorimetric measurement. For the bead assay, 24,000 of the G beads were incubated with 60 nM FPR and 75 nM $L^F$ in 10 µl assays in a 96 V-well plate on a vortex mixer for two hours, then the assays were diluted to 200 µl for flow cytometric measurement. Uncoated beads were used in an assembly assay, bar 1, or were coated with G protein βγ only and used in an assembly assay, bar 2. In bar 3, the standard assembly with Gαβγ was used; in bar 4, 0.1 mM GTPγS was added to the assembly assay; in bar 5, a fluoresceinated peptide, specific for the α4 integrin, see Chigaev et al. (2001), Real Time Analysis of the Affinity Regulation of Alpha 4-Integrin: The Physiologically Activated Receptor is Intermediate in Affinity Between Resting and Mn(2+) or Antibody Activation, J Biol Chem, 276, pp 48670–48678, the entire contents and disclosure of which is hereby incorporated by reference, was used in place of fluoresceinated formyl peptide; and in bar 6, membranes from cells containing no receptor were used instead of receptor-containing membranes. In FIG. 4B, fluorescent ligand ($L^F$, 40 nM) was used with an FPR-Gαi2 fusion protein (24 nM) to detect $L^F$R-αGβγ assembly on beads coated with Gβγ (1.4 pmol/assay). In bar 1, the beads were not coated with βγ; bar 2, with 0.1 mM GTPγS; bar 3, the standard assembly with Gβγ; bars 4–11, the indicated amounts of GTP were added to the standard assembly. In FIG. 4C, a fluorescent formyl peptide receptor $R^F$ (FPR-GFP, 200 nM) was used to detect the assembly of $LR^FG$ on DCNi beads in the presence of 300 nM L. Beads alone are shown in bar 1, or coated with βγ only in bar 2; the standard assembly, bar 3; bar 4, GTPγS was included in the assembly assay; and bar 5, no ligand was used in the assembly assay.

In FIG. 5A, the time of assembly $LR^FG$ was varied. In FIG. 5B, the amount of Gαβγ used to coat the beads was varied for $LR^FG$ assembly. In FIG. 5C, the concentration of ligand used was varied for $LR^FG$ assembly. In FIG. 5D, the concentration of FPR-GFP used was varied for $LR^FG$ assembly. In FIG. 5E, the concentration of FPR-αi2 used in the standard assembly (scheme of FIG. 3, complex C) was varied, using beads coated with Gβγ, for $L^FR$-αGβγ assembly.

FIG. 6A shows the determination of the dissociation constants of nonfluorescent ligands for receptor (R) by competition with $L^F$ in the spectrofluorimeter. Receptor (3 nM) and $L^F$ (5 nM) were incubated at 22° C. for two minutes, then an anti-FITC antibody was added as in FIG. 1A and analyzed to give an initial amount of $L^F$ bound, shown as the dotted line in FIG. 6A. Increasing amounts of nonfluorescent ligand were added to the R for two minutes, then $L^F$ was added for another two minutes to compete for the R, after which an anti-FITC antibody was added to determine the $L^F$ bound. $IC_{50}$ values were calculated from these curves, then $K_i$ values were calculated for each ligand, using the known [$L^F$], [R], and the $K_d$ of $L^F$ for R, from three experiments. FIG. 6B shows the determination of the $EC_{50}$ for nonfluorescent ligands for LRG formation. The standard LRG assembly assay was conducted with 30 nM $R^F$ and increasing amounts of each ligand as shown. $EC_{50}$ values were obtained from analysis of the curves, using three experiments for each.

In FIG. 8A, wild type FPR was used in the standard assembly to form $L^F$RG, and then the samples were diluted to 200 µl for kinetic flow cytometric measurement of bead fluorescence. Samples were applied to the cytometer for determination of initial bead fluorescence, then removed for addition of the GTPγS, after which the samples were returned to the cytometer for measurement of bead fluorescence (note five second gap). The filled circles represent no GTPγS addition. The initial open circles have been averaged over 10 sec, normalized to 1.0 and are shown as a single point for clarity at the point of GTPγS addition with the best fit to a two exponential decay shown as a line. In FIGS. 8B and 8C, six micron streptavidin-coated polystyrene beads were coated with biotinylated anti-FLAG antibodies as described in the experimental procedures discussed herein. The beads were then incubated with Gαi3β1γ2H6-FLAG (FIG. 8B) or Gαi3β4γ2H6-FLAG (FIG. 8C) in which the γ2 subunit was tagged with H6 and FLAG epitopes, as described in the experimental procedures discussed herein. Standard $L^F$RG assembly assays were conducted with (filled squares) or without (open circles) 0.1 mM GTPγS as indicated on the graphs, after which the 10 µl assays were diluted to 200 µl, and the bead fluorescence was measured by flow cytometry, as above. FIG. B required two exponential decays to obtain a good fit, whereas FIG. C shows a line fit to a single exponential decay.

In FIG. 9A, the LRG assembly requires ligand, receptor, and G protein. Assemblies on G protein coated Ni beads were conducted as described in the experimental procedures discussed in the present invention, except as noted, using 30 nM bAR-GFP or FPR-GFP, 1 mM ISO as the ligand, and 0.1 mM GTPgS as indicated. FIG. 9B shows that the ligand used and the amount of bAR-GFP used in the standard assembly assay were varied as shown. FIG. 9C shows that the amount of G protein used to coat the Ni beads was varied. FIG. 9D shows that the time of assembly was varied as shown.

DETAILED DESCRIPTION OF THE PREFERRED EMBODIMENT

Figure 1A:
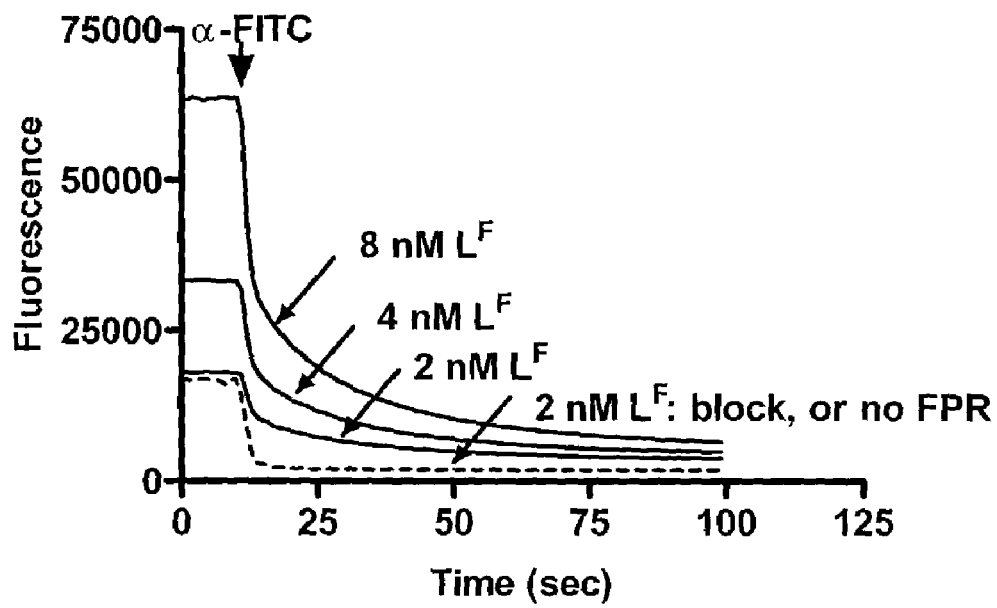
FIGS. 1A and 1B provide a graphical representation of soluble receptor determination.

It is advantageous to define several terms before describing the invention. It should be appreciated that the following definitions are used throughout this application.

Definitions

Where the definition of terms departs from the commonly used meaning of the term, applicant intends to utilize the definitions provided below, unless specifically indicated.

For the purposes of the present invention, the term "ligand" refers broadly to the conventional meaning of the term ligand i.e. a molecule, ion or atom that is capable of forming a complex with another molecule, ion or atom.

For the purposes of the present invention, the term "epitope-recognizing bead" refers to a bead bearing a chemical structure that binds to an epitope, or to any structure bearing that epitope.

For the purposes of the present invention, the term "epitope-bearing G protein subunit" refers to any $G\alpha$, $G\beta$, or $G\gamma$ that has any additional structure (the epitope) attached to it.

For the purposes of the present invention, the term "G protein heterotrimer" refers to any combination of ($G\alpha$+$G\beta$+$G\gamma$).

For the purposes of the present invention, the term "receptor" refers to a molecule on a cell that can bind another molecule (ligand) outside the cell.

For the purposes of the present invention, the term "G protein coupled receptor" refers to a seven transmembrane protein on a cell that can bind another molecule (ligand) outside the cell and a G protein inside the cell.

For the purposes of the present invention, the term "G protein coupled receptor molecular assemblies" refers to the binary ligand and receptor assembly, the ternary ligand-receptor-G protein assembly, or the ternary ligand-phosphorylated receptor-arrestin assembly.

Description

G protein coupled receptors form a ternary complex of ligand, receptor, and G protein heterotrimer (LRG) during signal transduction from the outside to the inside of a cell. The present invention provides a homogeneous, small volume bead-based approach compatible with high throughput flow cytometry, which allows evaluation of G protein coupled receptor molecular assemblies. Dextran beads were derivatized to carry chelated nickel to bind hexahistidine-tagged green fluorescent protein (GFP) and hexahistidine-tagged G proteins. Ternary complexes were assembled on these beads using fluorescent ligand with wild type receptor or a receptor-$G i\alpha 2$ fusion protein, and with a nonfluorescent ligand and receptor-GFP fusion protein. Streptavidin coated polystyrene beads used biotinylated anti-FLAG antibodies to bind FLAG-tagged G proteins for ternary complex assembly. Validation was achieved by showing time and concentration dependence of ternary complex formation. Affinity measurements of ligand for receptor on particles, of the ligand-receptor complex for G protein on the particles, and receptor-$G i\alpha 2$ fusion protein for $G\beta\gamma$, were consistent with comparable assemblies in detergent suspension. Performance was assessed in applications representing the potential of these assemblies for ternary complex mechanisms. First, the relationship was shown for a family of ligands between LR affinity and LRG affinity. Second, RGS4 and RGS8 were shown to alter the assembly characteristics of the receptor-$G i\alpha 2$ with $G\beta\gamma$ on the beads in a manner consistent with GTP turnover. Third, the potential of kinetic measurements to allow observation of individual steps of ternary complex disassembly was shown.

The present invention provides for preparing epitope-recognizing beads, which bind to epitope-bearing G protein subunits to form a bead-borne heterotrimeric G protein, solubilizing a GPCR, allowing the GPCR to bind to the bead-borne G protein in the presence of a ligand, and detecting the formation of a stable ligand-receptor-G protein (LRG) complex by flow cytometry. Beads may be used that recognize both the FLAG and six-histidine (H6) epitopes. G protein $\beta\gamma$ subunits tagged with both epitopes may be used, and supplemented with $\alpha$ subunits to form a heterotrimeric G protein ($\alpha\beta\gamma$) on the beads. Several methods may be used to detect LRG formation by flow cytometry: in a first method, soluble formyl peptide receptor (FPR) plus a fluorescent ligand are added to the beads, and in a second method, a chimeric soluble formyl peptide receptor-green fluorescent protein (FPR-GFP) plus a nonfluorescent ligand are added to the beads. FPR-G protein alpha subunit fusion proteins have also been detected using the methods of the present invention.

The epitope-tagged $\beta\gamma$ subunits assemble with $\alpha$ subunits to form heterotrimeric G protein on beads, and bind receptor in a dose dependent way. In one form of the assay, the binding of the receptor is visualized with fluorescent ligand. The complex dissociates with addition of GTP$\gamma$S, which shows that the complex involves a G protein. In a second form of the assay, the beads are incubated with a chimeric protein consisting of a GPCR and green fluorescent protein (GFP), and inclusion of ligand allows the chimeric GPCR-GFP to bind to the bead. This complex also dissociates in the presence of GTP$\gamma$S. In the third form of the assay, the beads are incubated with a chimeric protein consisting of a GPCR and G protein alpha subunit, and inclusion of a fluorescent ligand allows the chimeric receptor to bind to the bead. This complex also dissociates in the presence of GTP$\gamma$S.

The H6 and FLAG epitopes do not interfere with the assembly of the complex. Epitope-tagged $\alpha$ and $\beta$ subunits may be used according to the methods of the present invention and these approaches may be generalized to all epitopes.

Nickel chelate beads (latex, silica, and dextran) bind other proteins non-specifically, leading to high nonspecific, or background, signals; the smaller fluorescent ligand used in particular embodiments of the present invention has lower nonspecific binding. The FLAG epitopes were captured using a more complex bead, which was commercially coated with streptavidin, to which biotinylated anti-FLAG antibodies were bound. This second bead type generalizes the bead type and the epitope type, and may give improved (lower) background binding, in particular, when fluorescent proteins are used for detection.

Using chimeric GPCR-GFPs means that receptors that do not already have a fluorescent ligand available may also be used. This concept is generalizable to other GPCRs following the teachings of the present invention.

Using chimeric GPCR-GFPs for a receptor with no known ligand (an orphan receptor), one could screen for a ligand that would make the bead fluorescent, thereby defined as an agonist. Once this agonist is found, antagonists may be found by screening for agents that block the agonist-induced bead fluorescence. The human genome project produced many seven-trasnmembrane open reading frames, which presumably encode GPCR for which no ligand is yet known.

G proteins are expressed in bacteria in high concentration, with purification helped by the epitope tag, and are used at low concentration (nM), thus minimizing costs. The receptors may be prepared in bulk, by solubilizing crude membrane preparations from transfected cells, and are also used in low concentration.

Assays of the present invention may be multiplexed in several useful ways. For instance, it is possible to use colored beads, each bearing a different combination of G protein subunits ($\alpha,\beta,\gamma$), to determine the specificity of $\alpha\beta\gamma$ for a given LRG assembly. For example, chimeric FPR-$\alpha$i2 interacts well with $\beta 1\gamma 2$-bearing beads, but less well with $\beta 4\gamma 2$-bearing beads.

Applying other proteins to beads, such as a truncated arrestin, may provide for detection of receptors that were activated but not able to couple to G protein. Applying full length arrestin to beads could allow for the detection of phosphorylated receptors.

A goal of the present invention was to develop a general approach toward GPCR assays that would provide useful mechanisms in the broad field of high throughput screening for drug discovery.

Because GPCRs are prominent targets in drug discovery, the present invention provides generic assembly capabilities for GPCRs, using a homogeneous approach in which a flow cytometer may distinguish fluorescent molecules associated with a particle from those free in solution around the particle, see Sklar et al. (2002), Flow Cytometric Analysis of Ligand-Receptor Interactions and Molecular Assemblies, Ann Rev Biophys Biomol Struct, 31, pp 97–119, the entire contents and disclosure of which is hereby incorporated by reference. Based on solubilization in dodecyl maltoside, it has been shown that an epitope-tagged receptor could be associated with particles and analyzed by flow cytometry, using a fluorescent ligand to detect the assembled complex, see Sklar et al. (2000), Solubilization and Display of G Protein-Coupled Receptors on Beads for Real-Time Fluorescence and Flow Cytometric Analysis, Biotechniques, 28, pp 975–976, the entire contents and disclosure of which is hereby incorporated by reference. Such assemblies may further be adapted for analysis of ternary complex formation involving both signal transduction and termination partners, and these approaches would be compatible with high throughput flow cytometry, Kuckuck et al. (2001), High Throughput Flow Cytometry, Cytometry, 44, pp 83–90, the entire contents and disclosure of which is hereby incorporated by reference. This approach suffers from two important limitations. First, detecting signaling assemblies when the receptor is anchored to the particles is difficult. Second, in certain situations, detection of the assembly may require a fluorescent ligand to detect receptor affinity changes induced by subsequent receptor assemblies.

Both of the above-identified limitations have been addressed by the present invention. The present invention provides for the formation of high affinity complexes of the FPR with ligands on beads that have been coated with epitope-tagged G protein subunits. Ternary complexes have been assembled using three different receptor constructs (wild type, FPR-G$_i\alpha$ fusion, and FPR-GFP fusion), two types of epitope-tagged G proteins, two $\alpha$ and $\beta$ subunits, and two types of beads. Estimates of the affinities of ligand for receptor, ligand-receptor complex for G protein, and $\alpha$ for $\beta\gamma$ are appropriate for the detergent-solubililzed receptor. LR and LRG formation for a family of ligands have been evaluated, the rate at which different receptor forms dissociate was measured, and the impact of RGS on an assembly involving the Gi$\alpha$2-receptor fusion protein was evaluated.

Experimental Procedures

Reagents and Cell Culture. The cloning of the FPR, see Boulay et al. (1990), The Human N-Formylpeptide Receptor: Characterization of Two CDNA Isolates and Evidence for a New Subfamily of G-Protein-Coupled Receptors, Biochemistry, 29, pp 11123–11133, the entire contents and disclosure of which is hereby incorporated by reference, and its expression in U937 cells have been described, see Kew et al. (1997), Undifferentiated U937 Cells Transfected with Chemoattractant Receptors: a Model System to Investigate Chemotactic Mechanisms and Receptor Structure/Function Relationships, J Leukoc Biol, 61, pp 329–337, the entire contents and disclosure of which is hereby incorporated by reference. Plasticware was from VWR, and chemicals and reagents were from Sigma unless otherwise noted. The cells were grown in tissue culture treated flasks (Corning Inc.; Corning, N.Y.) in RPMI 1640 (Hyclone; Logan, Utah) with 10% fetal bovine serum (Hyclone), 2 mM glutamine, 10 mM HEPES, 10 units/ml penicillin and 2 µg/ml streptomycin. The cultures were grown at 37° C. with 5% $CO_2$ and passaged from subconfluent cultures every 3–4 days by reseeding at $2\times10^5$ cells/ml. The cells were expanded for membrane preparations in 1 liter baffled Pyrex spinner flasks by seeding at $2\times10^5$ cells/ml, equilibrated with 5% $CO_2$, then sealed and incubated at 37° C., with stirring. The cells were harvested when the density reached $10^6$ cells/ml. Receptor expression level decreased with passage, so freshly thawed cells were incubated with 10 nM fMLFK-FITC and sorted for the highest 5% expression to maintain 200,000–500,000 receptors/cell as needed, then frozen in aliquots for future use.

Generation of FPR-Gi$\alpha$2 and FPR-GFP Fusion Constructs. The human FPR (containing an EcoRI site and a NotI site embedded within the 5' and 3' primers, respectively) and rat Gi$\alpha$2 (containing a NotI site and an EcoRI site embedded within the 5' and 3' primers, respectively) were amplified by standard PCR protocols using Platinum™ Taq DNA polymerase (Perkin-Elmer; Norwalk, Conn.). The digested PCR products were ligated into EcoRI-digested and phosphatase-treated pSFFV.Neo and screened for orientation of the insert. Appropriate clones were confirmed by dideoxy sequence analysis. The final fusion protein contained three alanine residues between the last amino acid of the FPR and the first amino acid of the Gi$\alpha$2 protein-reading frame. A similar strategy was used to construct a plasmid to produce the FPR-GFP fusion protein using HindIII, NotI, and Xba, which again had three alanine residues between the last amino acid of the FPR and the first amino acid of the GFP (Clontech's EGFP, optimized for fluorescence using standard fluorescein filter sets; now part of BD Biosciences, Palo Alto, Calif.).

Membrane Preparation by Nitrogen Cavitation. The procedure was performed at 4° C. Cells were harvested by centrifugation at 450×g for 5 minutes and resuspended in cavitation buffer (10 mM HEPES, pH 7.3, 100 mM KCl, 3 mM NaCl, 3.5 mM $MgCl_2$, and 1× protease inhibitor cocktail 1 (Calbiochem; San Diego, Calif.)) at a density of $10^7$ cells/ml. This cell suspension was placed in a nitrogen bomb and pressurized to 450 p.s.i. for 20 minutes, after which the suspension was slowly released into a sample tube. Unbroken cells and nuclei were removed by centrifugation at 1000×g for 5 min. The membranes in the supernatant were pelleted by centrifugation twice at 135,000 ×g for 30 min, resuspended in buffer (25 mM HEPES, pH 7.5, 200 mM sucrose), and then aliquotted at $10^8$ cell equivalents in 0.5 ml, and stored at −80° C.

Solubilization of the FPR. An aliquot of membrane was thawed, 700 µl of buffer A (30 mM HEPES, pH 7.5, 100 mM KCl, 20 mM NaCl, 1 mM $MgCl_2$) was added, and the membranes were removed from the sucrose by centrifugation in a microfuge for 15 minutes. The supernatant was removed, the pellet was resuspended in 220 µl of buffer A by 10 passes back and forth through a 25G needle, 25 µl of 10% dodecyl maltoside and 2.5 µl of 100×protease inhibitor cocktail were added, and the suspension was gently mixed for 2 hours at 7° C. The unsolubilized material was removed by centrifugation as above for 15 minutes, giving a supernatant of solubilized FPR at $4\times10^8$ cell equivalents/ml (~5 mg/ml protein), and used within 6 hours. Solubilization was essentially 100%, so that 150,000 receptors/cell resulted in about 100 nM soluble FPR using this procedure. For FPR-GFP ($R^F$) preparations, 2 μl of $10^{-4}$ M ligand (fMLFFGGK) was added to 200 μl of the preparation when desired to give quantitative conversion of $R^F$ to $LR^F$. For FPR, $L^F$ (fMLFF-FITC) was added when desired at greater than the concentration of receptor to ensure nearly quantitative conversion of R to $L^F R$, while keeping the concentration of free ligand low, to minimize nonspecific binding to the beads. The solublilized receptor preparation retained >90% activity after freezing at −80° C.

Use of Formyl Peptides. $L^F$ (fMLFK-FITC) was obtained from Bachem (King of Prussia, Pa.). Typically, 1 mg was dissolved in 10 ml of methanol, and 30 μl of the solution at about 0.1 mM was diluted in 3 ml of buffer A with 0.1 mg/ml BSA to obtain the absorbance at 495 nm. The concentration of $L^F$ was calculated using an extinction coefficient of 76,000 $M^{-1}cm^{-1}$. The methanol solution was aliquotted into microfuge tubes to give $10^{-8}$ mol of $L^F$, and dried in a Speedvac. These aliquots were stored at −20° C., dissolved in 10 μl of DMSO to give $10^{-3}$ M $L^F$, then diluted at least 100-fold in buffer A with 1 mg/ml BSA to give $10^{-5}$ M $L^F$.

L (fMLFFGGK) was synthesized by Commonwealth Biotechnologies, Inc. (Richmond, Va.). Dry peptide (8.2 mg) was dissolved in a final volume of 1 ml of acetic acid/water: 100 μl of acetic acid dissolved the powder, then 900 μl of 50% acetic acid was added. This was diluted 100-fold into buffer A, which was brought back to pH 7.5 with NaOH, giving $10^{-4}$ M L. It was aliquotted into 1 ml and 10 μl aliquots, stored at −20° C., and thawed fresh each day.

Synthesis of Dextran Chelate Nickel (DCNi) Beads. Superdex Peptide beads, a crosslinked agarose/dextran matrix with an exclusion limit of 7,000 Daltons and an average size of 13 μm, were removed from a packed column purchased from Amersham Pharmnacia Biotech. (Superdex 30 Prep Grade beads, average size 34 μm, are also compatible with flow cytometric analysis.) The beads were activated with a water-soluble bis-epoxide, and then coupled to a chelator that contained an amino group, see Sundberg L and Porath J (1974), Preparation of Adsorbents for Biospecific Affinity Chromatography: Attachment of Group-Containing Ligands to Insoluble Polymers by Means of Bifunctional Oxiranes, J Chromatogr, 90, pp 87–98, the entire contents and disclosure of which is hereby incorporated by reference. 12 ml of a 50% slurry of beads was reduced to a wet cake by vacuum filtration using a 60 ml coarse sintered glass funnel, and then washed three times with 50 ml of water to remove the ethanol in which the beads were supplied. The wet cake was transferred to a 25 ml Erlenmeyer flask, the funnel was rinsed with 5 ml of water, and this rinse was added to the flask. One ml of 5 M NaOH, 10 mg of $NaBH_4$, and 5 ml of 1,4-butanediol diglycidyl ether (Sigma) were then added, and the flask was rotated to keep the beads in suspension for 8 hrs at 37° C.; some bubbling occurred in the first hour. The beads were washed by vacuum filtration twice with water, twice with phosphate buffered saline (PBS), twice with water again, then stored for up to one week at 4° C., or for two months dried at 4° C. One settled volume of these epoxy-activated beads was coupled with one volume of the chelator $N_\alpha,N_\alpha$-bis(carboxymethyl)-L-lysine (Fluka) in 0.2M $Na_2CO_3$, pH 11, adjusting the pH again after addition to the beads. 2.5 mM, 25 mM, and 250 mM chelator was used in three different reactions to obtain different substitution levels on the beads. The coupling proceeded at 22° C. overnight with gentle mixing to keep the beads in suspension. The beads were washed as above and then treated with ten volumes of 0.1M $NiCl_2$ for 1 minute in column or batch mode; the two highest-substituted batches became visibly blue/green, while the lightly-substituted batch remained white. The beads were rinsed with water and PBS. Atomic absorption analysis of the three samples showed the content of Ni to be 1.5 mM, 16 mM, and 30 mM for the settled beads: substitution appeared proportional to the concentration of amino compound up to 25 mM in the reaction, then began to saturate.

Coating DCNi beads With H6-Tagged G Proteins. N-terminal hexahistidine-tagged γ2 subunit (H6γ2) CDNA was created by standard recombinant DNA techniques. A β1H6γ2 dimer was produced by coexpression of a β1 subunit and a H6γ2 subunit in Sf9 insect cells, and the dimer was purified essentially as previously described, see Kozasa T and Gilman A G (1995), Purification of Recombinant G Proteins from Sf9 Cells by Hexahistidine Tagging of Associated Subunits, Characterization of Alpha 12 and Inhibition of Adenylyl Cyclase by Alpha z, J Biol Chem, 270, pp 1734–1741, the entire contents and disclosure of which is hereby incorporated by reference, using a Ni chelate column followed by a Mono S column (Amersham Biosciences). The β1H6γ2 preparation was 46 μM, and 14 μl was incubated with 15 μl of 42 μM αi3 subunit (Calbiochem) and 44 μl of G buffer (0.1% dodecyl maltoside, 30 mM HEPES, pH 7.5, 100 mM KCl, 20 mM NaCl, 1 mM $MgCl_2$, and 1 mM DTT) for 5 minutes on ice to allow the G protein heterotrimer to form, then frozen in 2 μl (17 pmol) aliquots. After thawing, 2.5 μl of a 50% slurry of DCNi beads ($2.5 \times 10^8$ beads/ml) was added, and the volume was brought to 100 μl with G buffer. The beads were kept suspended with rotation at 7° C. for one hour, then pelleted by centrifugation and brought to 50 μl with G buffer. This gave $1.2 \times 10^7$ beads/ml, nominally coated with 18 million G protein αβH6γ per bead, with an unknown amount left on the beads in an active orientation (for comparison, assuming that random fall results in about 50% coverage, one expects about 7 million BSA molecules per 13 μm sphere); 2 μl of bead suspension was used per 10 μl assay, consuming about 0.7 pmol Gαβγ per assay on 24,000 beads. The beads retained more than 90% of their binding activity after freezing at −80° C. When the FPR-αi2 fusion protein was used for an assembly, only the β1H6γ2 dimer was used to coat the DCNi beads as above.

Figure 6A:
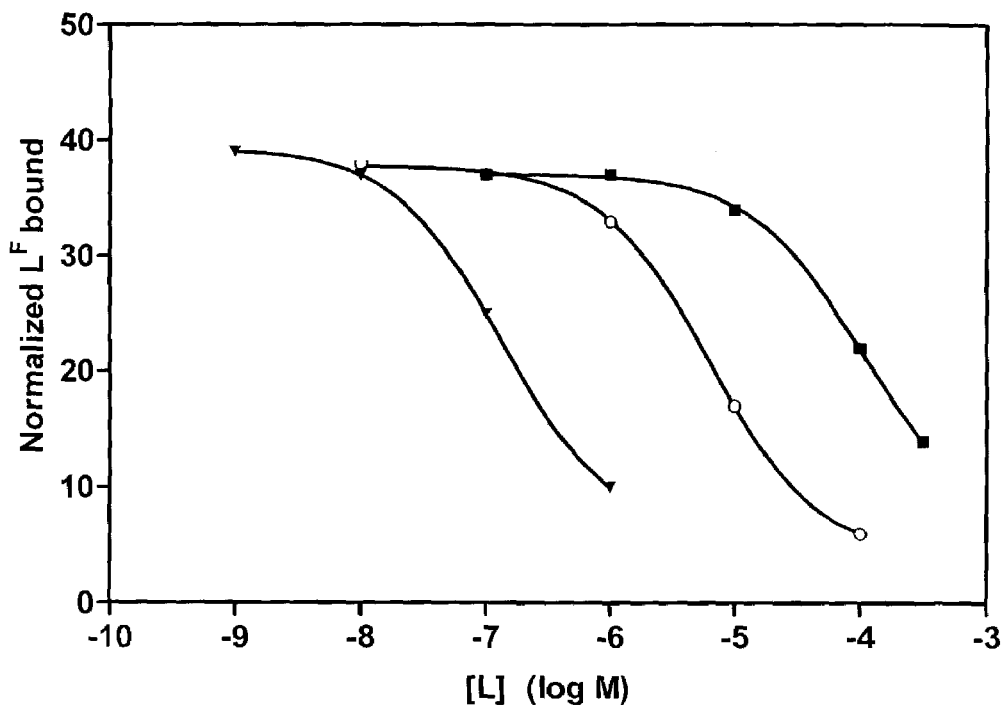
FIGS. 6A and 6B show the determination of interaction constants for nonfluorescent ligands. Triangles represent fMLFF, circles represent fMLF, and squares represent fML.

Standard LRG Assembly Assay. The standard 10 μl assay consisted of 2 μl of water or $10^{-4}$M GTPγS, 6 μl of soluble receptor preparation with or without ligand, and 2 μl of beads prepared as above, with 0.7 pmol G protein used per assay, and an unknown fraction left on the beads in the proper orientation. For FPR and R-αi2 assemblies, $L^F$ (fMLFK-FITC) was added in excess of receptor to ensure that essentially all the receptor was bound. For FPR-GFP assembly, $10^{-6}$ M L (fMLFFGGK) was added to the receptor preparation to ensure that essentially all the receptor was bound. Each mixture was mixed by pipetting to ensure a uniform starting suspension of the beads in 96 V-well plates (Costar), and then mixed at low speed on a vortex mixer at 7° for two hours. The 10 μl assays were individually brought to 200 μl with 0.1% dodecyl maltoside in buffer A in 12×75 mm tubes for flow cytometric measurement of fluorescence of the beads. LRG assembly was defined as the difference between fluorescence without GTPγS and that with GTPγS. All determinations were done in duplicate. For assays with the FPR-αi2 chimera, a low amount of GTP was present (vide infra), and for the demonstration of RGS activity, both GTP and RGS proteins were added at the concentrations shown in FIGS. 6A and 6B, see also Lan et al. (2000), Rapid Kinetics of Regulator of G-Protein Signaling (RGS)-Mediated Galphai and Galphao Deactivation: Galpha Specificity of RGS4 and RGS7, J Biol Chem, 275, pp 33497–33503, the entire contents and disclosure of which is hereby incorporated by reference.

Flow Cytometry Analysis and Calibration. Flow cytometry was carried out using FACScan cytometers (Becton-Dickinson), obtaining 3,000 gated events (see FIG. 2A for a typical gate of the DCNi beads) for a sample to obtain a mean channel fluorescence (MCF). These numbers were converted to the mean equivalent of soluble fluorophores on a bead using calibrated beads (Bangs Labs). The number of receptors on a bead was determined by multiplying this by 1.22 to reflect the smaller fluorescence of conjugated fluorescein compared to free fluorescein, see Buranda et al. (2001), Detection of Epitope-Tagged Proteins in Flow Cytometry: Fluorescence Resonance Energy Transfer-Based Assays on Beads with Femtomole Resolution, Anal Biochem, 298, pp 151–162, the entire contents and disclosure of which is hereby incorporated by reference. Since GFP gave a lower molar fluorescence (quantum yield) than normal $L^F$, the mean equivalent of soluble GFP fluorophores was multiplied by 2.1 to calculate the number of GFP molecules on a bead.

Coating Streptavidin-Coated Beads With Biotinylated Anti-FLAG Antibody and FLAG-Tagged G Proteins. Twenty microliters of 6.2 µm diameter streptavidin-coated polystyrene beads at $4\times10^7$ beads/ml (Spherotech Inc., Libertyville, Ill.) were mixed with 20 µl of 1 mg/ml biotinylated anti-FLAG antibody (Sigma) for 2 hours at 4° C., and then washed three times in buffer to give $\sim 9\times10^6$ FLAG-FITC binding sites per bead at 4,000 beads/µl, see Buranda et al. (2001), Detection of Epitope-Tagged Proteins in Flow Cytometry: Fluorescence Resonance Energy Transfer-Based Assays on Beads with Femtomole Resolution, Anal Biochem, 298, pp 151–162, the entire contents and disclosure of which is hereby incorporated by reference. G protein γ2-H6-FLAG subunits were co-expressed with β4 subunits in Sf9 cells, which were extracted as described, see McIntire et al. (2001), The G Protein Beta Subunit is a Determinant in the Coupling of Gs to the Beta 1-Adrenergic and A2a Adenosine Receptors, J Biol Chem, 276, pp 15801–15809, the entire contents and disclosure of which is hereby incorporated by reference. The extract was loaded on a 3 ml FLAG column (Sigma) and eluted with FLAG peptide according to the manufacturer's instructions. The eluate was immobilized on a 4 ml nickel column, washed with increasing concentrations of salt and detergent, then eluted with imidazole. The eluate was immobilized on a 15Q column (Amersham Biosciences), eluted with salt, concentrated with a Centricon 30, aliquotted, and stored at −80° C. This βγ preparation was combined with equimolar αi3 (Calbiochem) as above. Fifty microliters of the beads were mixed with 1 µl of 3.4 µM αi3β4γ2-FLAG-H6 for 1 hour, spun, and resuspended in 40 µl buffer, to give beads nominally coated with nine million G protein αβγ per bead; 2 µl of this suspension was used per assay, ~0.17 pmol per assay, on 10,000 beads. These beads are smaller than the DCNi beads, and easier to keep in suspension.

Kinetic LRG Disassembly. LRG was assembled according to one of the three methods above, depending on the receptor type. The 10 µl assay was brought to 200 µl as usual at the flow cytometer and an initial fluorescence was recorded for 20 seconds, then the tube was removed, 2 µl of 0.01 M GTPγS or 6 µM anti-FITC antibody was added at 25 seconds, and the tube was put back on the flow cytometer for dynamic measurement of fluorescence. A 2 mm×5 mm stir bar (Bel-Art; Pequaimock, N.J.) was driven by a magnetic stirrer brought near the tube to keep the beads in suspension. The time course data were converted to ASCII format using the Facsquery program (developed by Bruce Edwards), which puts the raw data into bins of the desired time period with an MCF for each bin in an Excel file. Dissociation curves of this series of MCF values were analyzed using Prism (Graphpad Software; San Diego, Calif.).

Spectrofluorimetric Analysis of Soluble Complexes. Fluorescence was measured with an SLM 8000 spectrofluorimeter (SLM Instruments, Inc.) using the photon counting mode. The sample holder was fitted with a cylindrical cuvette adapter, which allowed the use of 200 µl samples in 7mm ×45 mm cylindrical cuvettes (Sienco; Wheat Ridge, Colo.), stirred with 2×5 mm stir bars (Bel-Art). Excitation was at 490 nm, and stray light was reduced with a 490+/−10 nm filter (Corion; now part of Spectra-Physics, Franklin, Mass.). Emission was monitored using a 520+/−10 nm filter (Corion) and a 500 nm long-pass filter (Kopp; Pittsburg, Pa.). Additions to samples during kinetic measurements were made through an injection port on the top of the sample holder with 10 µl glass syringes (Hamilton; Reno, Nev.). For each concentration of fluorescent ligand used, a sample of solubilized proteins from membranes containing receptor and membranes without receptor were measured, typically 5 µl of a 60 nM R preparation to give 3 nM R, as shown in FIG. 1A for 2 nM $L^F$. Although these lines have been shifted in this figure for clarity, inspection showed the point at which the receptor-containing curve deviated from the control curve, below which represented the amount of the 2 nM ligand which was bound to the receptor (in this case, 0.7 nM), and above which represented the ligand which was free (in this case, 1.3 nM): these two numbers gave the first point in FIG. 1B. For accurate analysis, and for kinetic dissociation analysis, the percent of the control curve corresponding to the percent free ligand was subtracted from the receptor-containing curve.

Results

Figure 1B:
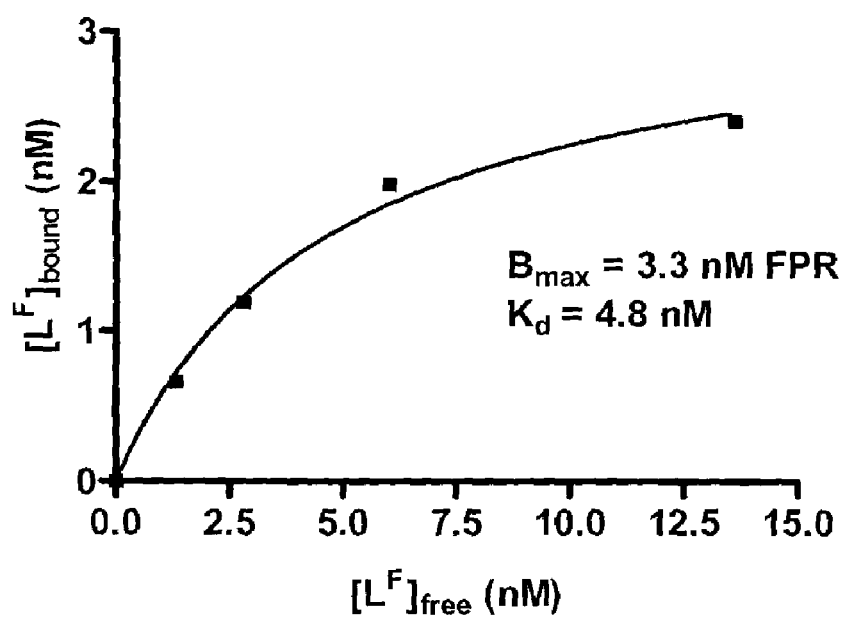

Soluble FPR Assay. The presence of LR and LRG complexes in solution has been shown using a fluorimetric assay in which FPR are quantitatively solubilized, see Bennett et al. (2001), Real-Time Analysis of G Protein-Coupled Receptor Reconstitution in a Soubilized System, J Biol Chem, 276, pp 22453–22460; Bennett et al. (2001), Partial Plosphorylation of the N-Formyl Peptide Receptor Inhibits G Protein Association Independent of Arrestin Binding, J Biol Chem, 276, pp 49195–49203; Key et al. (2001), Regulation of Formyl Peptide Receptor Agonist Affinity by Reconstitution with Arrestins and Heterotrimeric G Proteins, J Biol Chem, 276, pp 49204–49212; and Sklar et al. (2000), Solubilization and Display of G Protein-Coupled Receptors on Beads for Real-Time Fluorescence and Flow Cytometric Analysis, Biotechniques, 28, pp 975–976, the entire contents and disclosures of which are hereby incorporated by reference. The detection of LR in a spectrofluorimeter was accomplished with a fluoresceinated ligand, formyl-MLFK-FITC ($L^F$), and an anti-FITC antibody, which quenched the fluorescence of the FITC on the ligand about 91% when it was bound. Since the FPR quenched the fluorescence of the ligand minimally, addition of ligand to a detergent-solubilized receptor preparation gave a high initial fluorescence, some of which was due to bound $L^F$, and some of which was due to free $L^F$ (FIG. 1A). The free ligand and bound ligand were discriminated using an antibody to fluorescein that rapidly quenched only the free ligand. The dissociation halftime for $L^F$ was 14 seconds at room temperature. FIG. 1B shows a plot of the data from FIG. 1A in the form of a ligand-binding curve, from which one can obtain a $K_d$ of 4.8 nM, and a $B_{max}$ of 3.3 nM FPR. The dissociation rate, its insensitivity to guanine nucleotide (not shown), and $K_d$ were consistent with the LR but not the LRG form of the receptor.

Soluble Receptor Display on Beads. In previous studies, for example in Sklar et al. (2000), Solubilization and Display of G Protein-Coupled Receptors on Beads for Real-Time Fluorescence and Flow Cytometric Analysis, Biotechniques, 28, pp 975–976, the entire contents and disclosure of which is hereby incorporated by reference, commercial porous silica particles intended for protein purification were used (Qiagen; Valencia, Calif.). Although they could bind several million receptors on an average size particle, the particles were heterogeneous in size, appeared to break under gentle stirring as monitored by flow cytometry light scatter patterns, and settled rapidly in aqueous media. Therefore, a hydrophilic particle, DCNi, was prepared as described in the experimental procedures discussed herein. Hexahistidine-tagged enhanced green fluorescent protein (H6-GFP; generously supplied by Dr. John Nolan), see Lauer S A and Nolan J P (2002), Development and Characterization of Ni-NTA-Bearing Microspheres, Cytometry, 48, pp 136–145, the entire contents and disclosure of which is hereby incorporated by reference, was used initially to help determine the suitability of the DCNi beads for display of proteins in a flow cytometer. This H6-GFP was found to have a molar fluorescence, or quantum yield, in solution of 60% compared with our standard fluoresceinated formyl peptide ligand, formyl-MLFK-FITC.

Figure 2A:
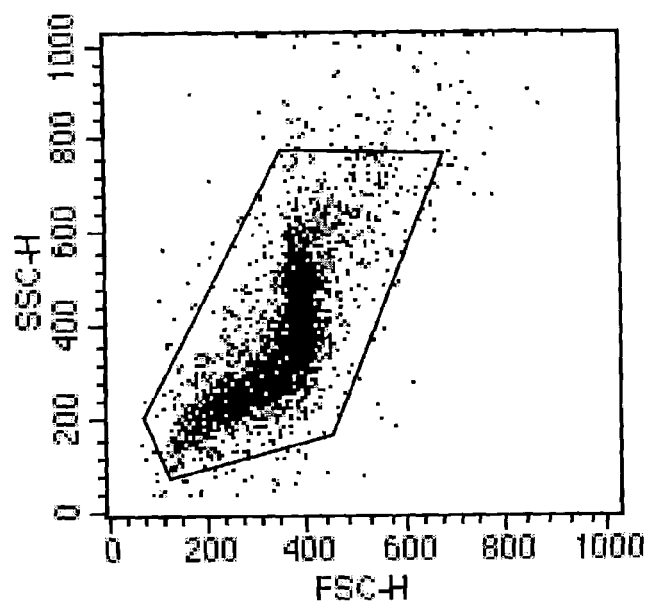
FIGS. 2A, 2B, 2C, 2D, 2E and 2F show the characterization of dextran chelate nickel (DCNi) beads by flow cytometry.
Figure 2B:
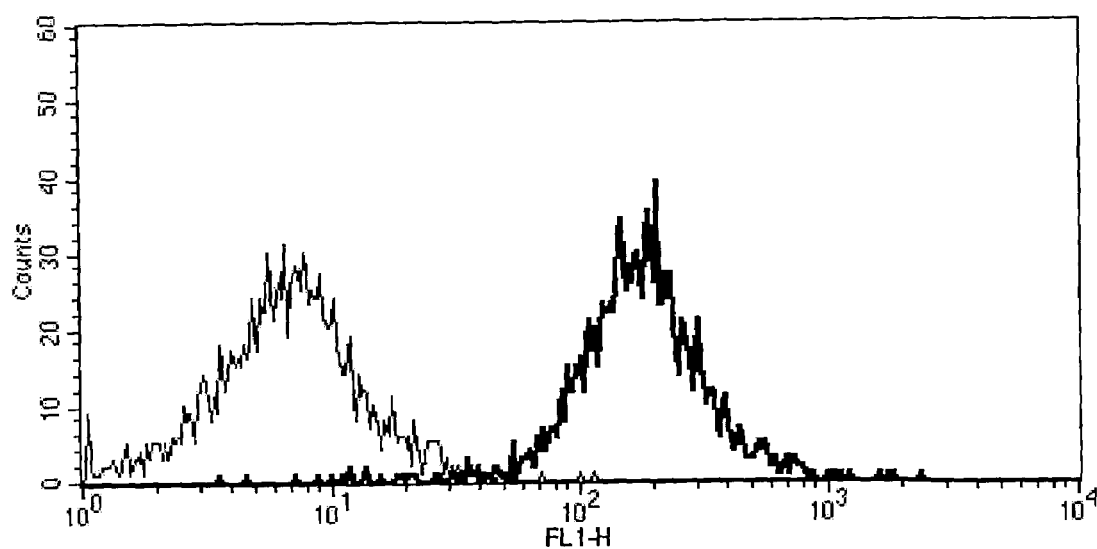
Figure 2C:
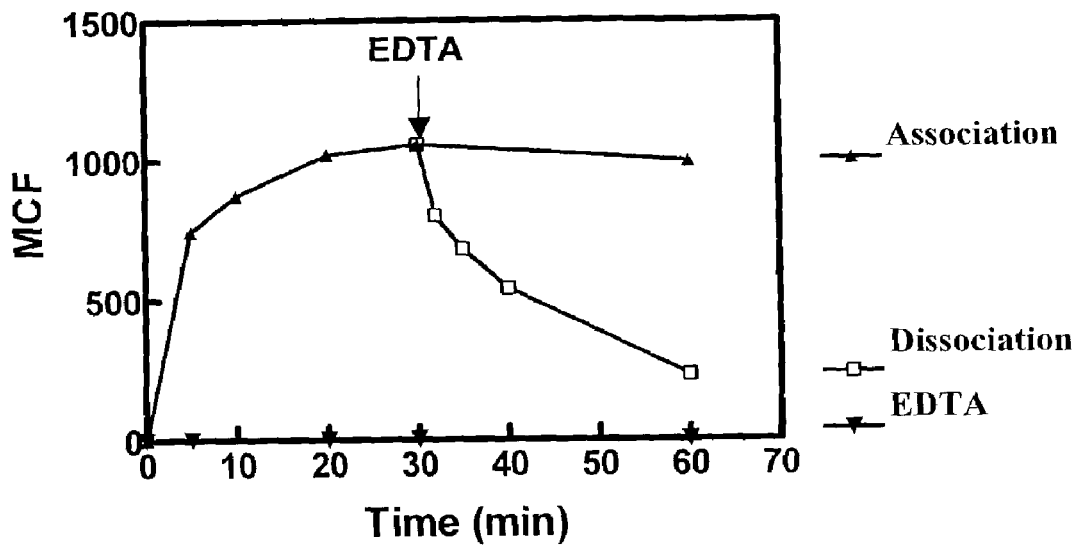

DCNi beads of the lowest level of substitution were suspended in phosphate-buffered saline at 50,000 beads/ml at 4° C., with or without 10 mM EDTA. FIG. 2A is a dot plot of these beads' forward scatter vs. side scatter, which vary slightly more than those of a cell population. FIG. 2B displays a histogram of unstained and stained beads. The kinetic data of FIG. 2C show that in the absence of EDTA, addition of 10 nM H6-GFP resulted in maximal bead fluorescence after about 20 minutes, and displayed about 5 million fluors per bead by comparison with standardized fluorescent microspheres. A portion of these beads was brought to 10 mM EDTA at 30 minutes, and the H6-GFP on the beads was reduced by 80% after 30 minutes. The stable binding of this platform is demonstrated in FIG. 2D, in which the H6-GFP remained on the beads for five washes over two hours, following which the H6-GFP was displaced by 10 mM EDTA as before. Nickel chelate beads have high nonspecific binding in general, and the presence of other protein or detergent (1 mg/ml BSA or 0.1% Tween-20, respectively) reduced the binding of H6-GFP by 80% (data not shown).

Figure 2D:
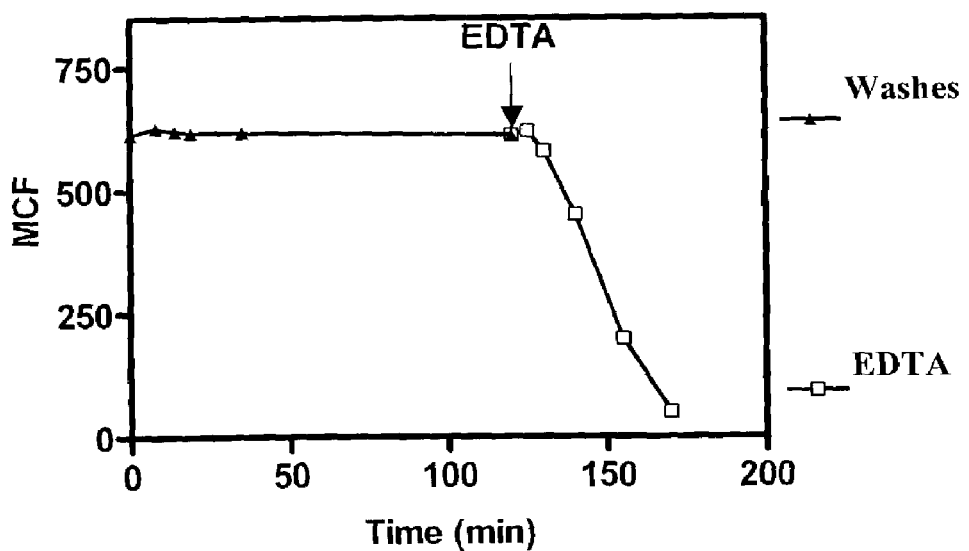
Figure 2E:
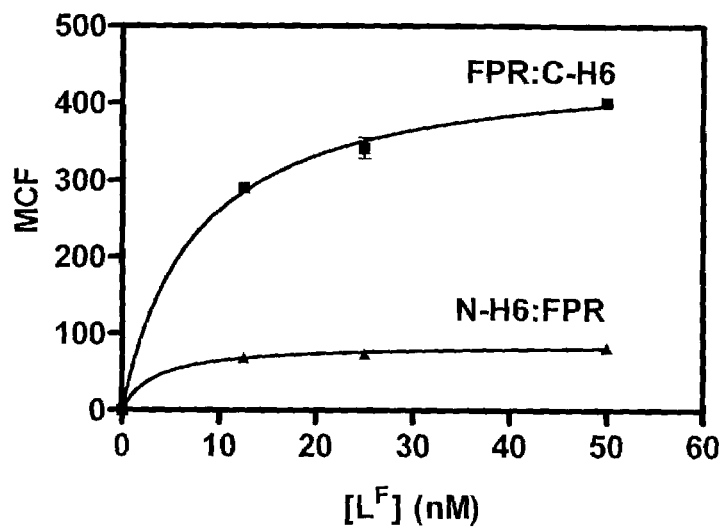
Figure 2F:
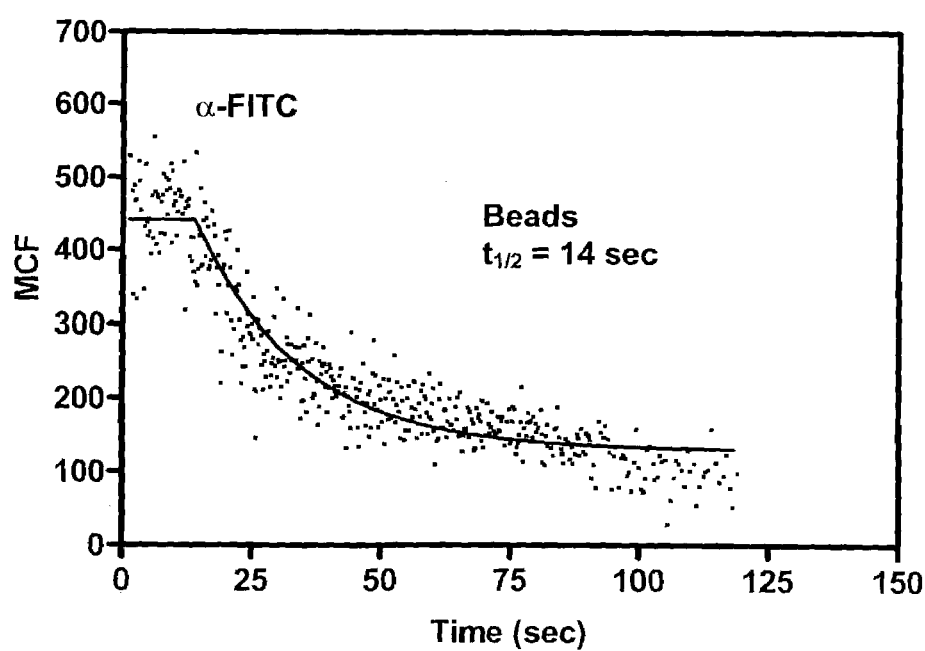

As described previously in Sklar et al. (2000), Solubilization and Display of G Protein-Coupled Receptors on Beads for Real-Time Fluorescence and Flow Cytometric Analysis, Biotechniques, 28, pp 975–976, the entire contents and disclosures of which are hereby incorporated by reference, several million six histidine-tagged receptors could bind to a porous silica nickel chelate bead, in an LR form with a $K_d$ similar to the soluble receptor in detergent. DCNi beads were able to bind ~400,000 formyl peptide receptors with a C-terminal hexahistidine tag (FPR:C-H6), as detected by $L^F$ (FIG. 2E). The amount of receptor bound was a function of the position of the tag, with the FPR:C-H6 consistently binding more than the FPR with an N-terminal hexahistidine tag (N-H6:FPR). Although there was 1.9 times the concentration of FPR:C-H6 compared to N-H6:FPR in this experiment, the FPR:C-H6 displayed 5 times the binding of N-H6:FPR. The binding of receptor in this complex mixture of solublilized proteins was very slow, and continued to increase even after the seven hour data obtained in FIG. 2E (data not shown). The $K_d$ for ligand binding was estimated to be 8 nM and the ligand dissociation rate was similar on beads to the rate in detergent solution, with a 14 second halftime of dissociation (FIG. 2F). While the receptor appeared to behave normally, addition of heterotrimeric G did not alter the ligand $K_d$ or dissociation rate using the N-H6:FPR, which was expected to have a free binding site for G protein while bound to the beads. Therefore, the route to ternary complex assembly was followed as described below.

Figure 3:
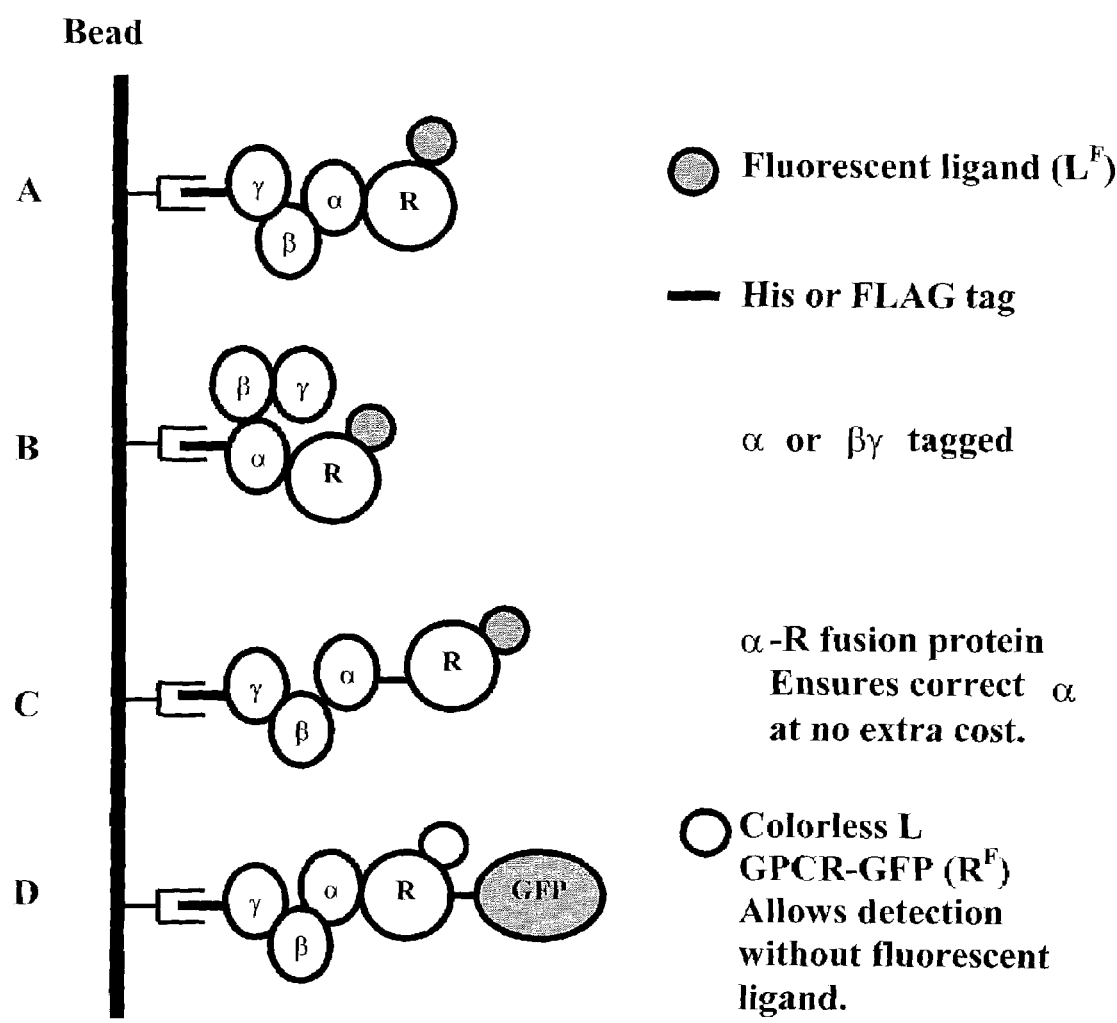
FIG. 3 shows ligand-receptor-G-protein complex (LRG) assembly schematics. Complex A shows fluorescent ligand, wild type receptor, epitope tagged Gβγ, and Gα bound to a derivatized bead; complex B is the similar to complex A, except with the epitope on the Gα subunit; complex C shows fluorescent ligand, receptor-Gα fusion protein, and epitope tagged Gβγ bound to the bead; complex D shows a colorless ligand, receptor-GFP fusion protein, epitope tagged Gβγ, and Gα bound to the bead. In each case, a receptor without ligand would not bind the bead significantly.

Detection of $L^F$RG Complexes on Beads. As structural analysis and functional studies suggested that the amino terminus of the γ subunit could be modified without interfering with ternary complex assembly, see McIntire et al. (2001), The G Protein Beta Subunit is a Determinant in the Coupling of Gs to the Beta 1 -Adrenergic and A2a Adenosine Receptors, J Biol Chem, 276, pp 15801–15809, the entire contents and disclosure of which is hereby incorporated by reference, purified, epitope-tagged G-proteins were used to coat the particles. FIG. 3 shows several complementary attachment schemes: wild type receptors binding to bead-associated subunits with fluorescent ligand detection (complexes A and B); Giα2-receptor fusion protein detected with fluorescent ligand (complex C); and receptor-GFP fusion protein detected directly (complex D).

Figure 4A:
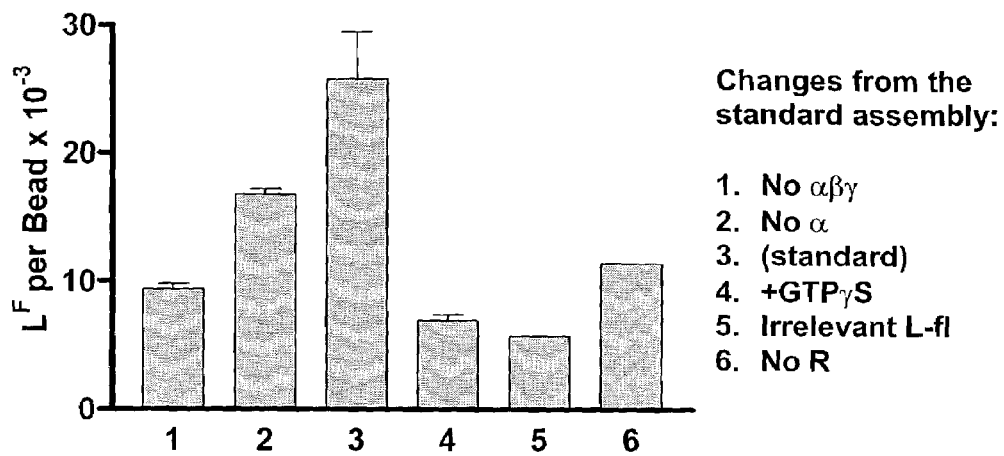
FIGS. 4A, 4B and 4C show results from a calibrated LRG assembly with three receptor constructs on DCNi beads.

To prove the concept of assembly on beads, fluorescent ligand, $L^F$, was used to form $L^F$RG on the beads (FIG. 3, complex A). G protein coated beads (G beads) were prepared and washed as described in the experimental procedures discussed herein, giving beads coated with αi3β1H6γ2 (18 million αβγ were provided per bead, and based on the solubilized receptor, perhaps 400,000 were in proper orientation). Evidence that fluorescence on the beads was due to $L^F$RG included the requirement that $L^F$, R, and G were all necessary for fluorescence over nonspecific, background fluorescence. As shown in FIG. 4A, uncoated beads gave a background binding equivalent to about 9,000 fluorophores. The binding doubled when βγ was on the beads, and tripled when αβγ was on the beads. These data may be interpreted to indicate that the αβγ beads, having the highest fluorescence, had everything necessary for $L^F$RG formation, while the βγ beads, probably with endogenous αi supplied in the crude solubilized membrane FPR preparation, gave an intermediate, weaker signal. The addition of GTPγS, which should dissociate α from βγ and R, resulted in only background fluorescence (similar to unlabeled beads) both with βγ and αβγ beads, as expected. This observation rules out binding of $L^F$R to βγ alone and indicates that an α subunit, either exogenous or in the receptor preparation, may be required. Use of an irrelevant fluorescent peptide, specific for the α4 integrin, see Chigaev et al. (2001), Real Time Analysis of the Affinity Regulation of Alpha 4-Integrin: The Physiologically Activated Receptor is Intermediate in Affinity Between Resting and Mn(2+) or Antibody Activation, J Biol Chem, 276, pp 48670–48678, the entire contents and disclosure of which is hereby incorporated by reference, instead of a fluorescent formyl peptide, also showed only nonspecific binding. Substitution of parental cell extracts that contained no receptor showed increased binding, attributed to the fact that free ligand was higher in the absence of FPR, which binds the majority of the total ligand; a high concentration of the free ligand alone gives a nonspecific signal of this magnitude (data not shown). Thus, $L^F$, R, and G were all necessary for the specific fluorescent signal, defined as bar 3 minus bar 4. Under more nearly optimal conditions, signal to background levels have been observed as high as 4/1 in this assembly with 30,000 ternary complexes per particle.

Figure 4B:
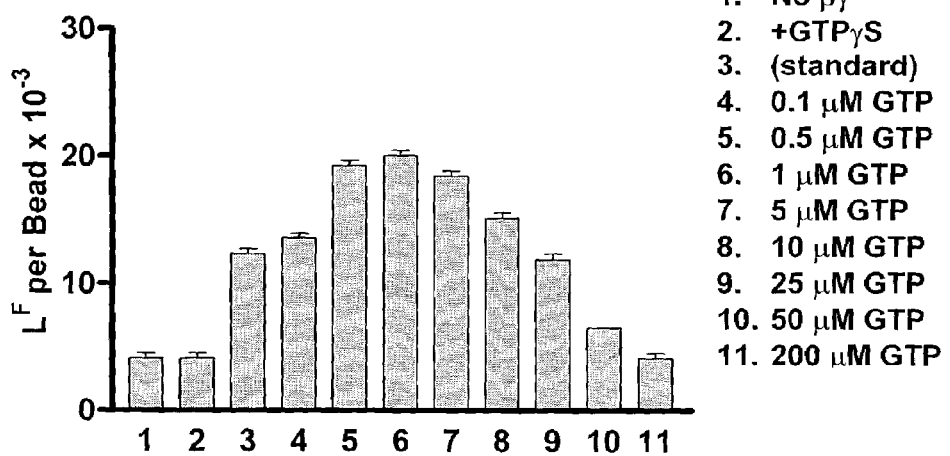
Figure 7:
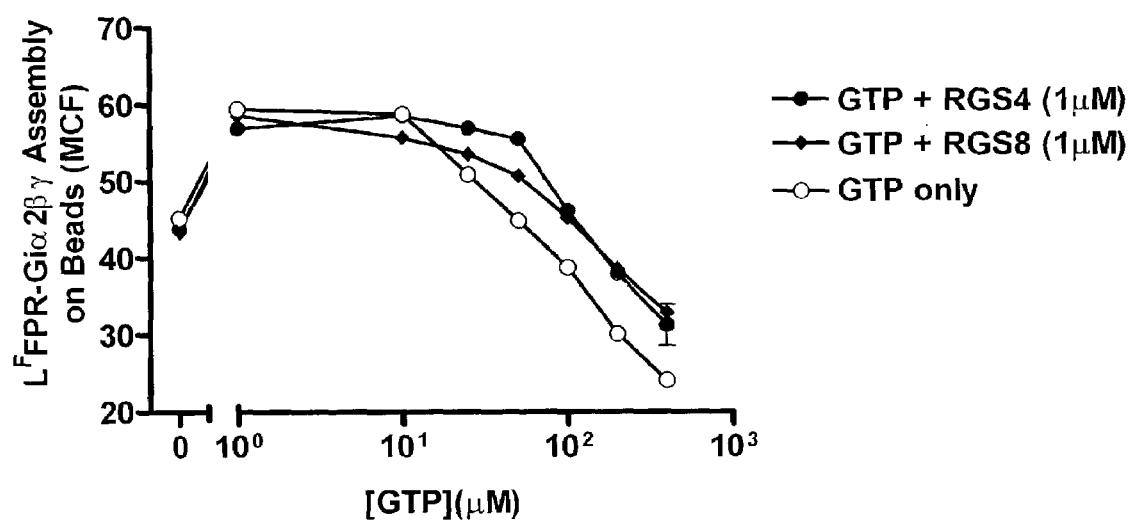
FIG. 7 shows the results of a regulator of G protein signaling (RGS) activity assay on beads. FPR-αi2 (R-α) was used in the standard assembly assay with fluorescent ligand (see FIG. 3, complex C), and with the amounts of GTP and RGS shown in FIG. 7, using beads coated with Gβγ. Bead fluorescence was measured as previously described.

Detection of $L^F R$-αGβγ Complexes on Beads. An FPR-αi2 fusion protein was generated as described in the experimental procedures discussed herein, and solubilized. With this construct (FIG. 3, complex C), it was anticipated that endogenous βγ in the solubilized fusion protein preparation might bind to FPR-αi2 to form LRG complex in solution (Shi et al., submitted), and prevent the FPR-αi2 from binding the βγ on the beads. Therefore, the ability of GTP to promote the dissociation of FPR-αi2 from endogenous βγ was examined, and as the GTP was hydrolyzed, the ability of more FPR-αi2 to bind the βγ beads was examined. βγ beads (24,000) were mixed with 24 nM FPR-αi2 and 40 nM $L^F$ as in the standard protocol, with GTP as indicated, in FIG. 4B. Uncoated beads, and beads coated with βγ but incubated in the presence of GTPγS, gave background binding equivalent to about 5,000 fluors. Assembly in the absence of GTP showed about 12,000 fluors, while assemblies in the presence of 0.1 μM to 10 μM GTP all showed up to 20,000 fluors. Assemblies conducted in the presence of yet higher amounts of GTP showed less bead fluorescence than assembly with no GTP, consistent with excess GTP remaining after the incubation. 1 μM GTP was optimal for the highest binding on the beads and the highest specific signal, defined as bar 6 minus bar 2. Additional experiments with RGS suggested that GTP consumption played a role in ternary complex assembly (see FIG. 7). The best total fluorescence to background ratio (bar 6 compared to bar 2) was 2.7/1, similar to that observed for the wild type receptor above.

Figure 4C:
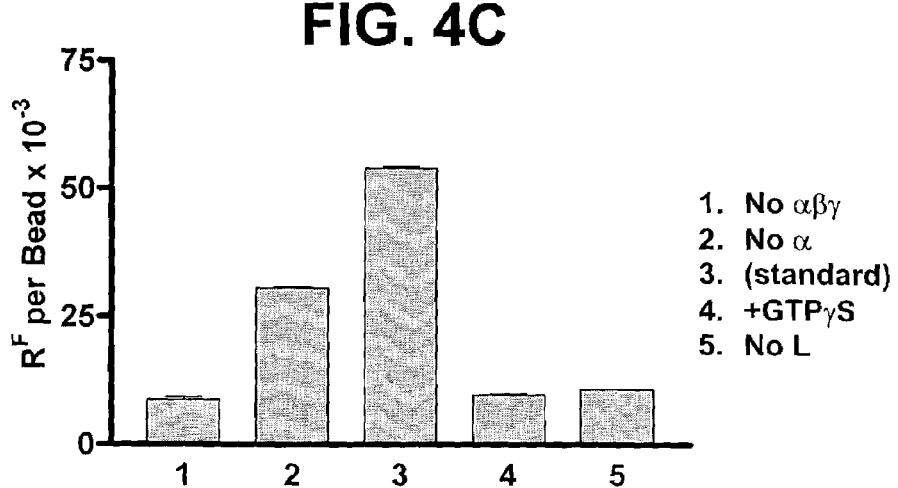

Detection of $LR^F G$ Complexes on Beads. The third assembly used a fusion protein of FPR with enhanced green fluorescent protein (FIG. 3. complex D: FPR-GFP, or $R^F$). The fusion protein was expressed and solubilized as described in the experimental procedures discussed herein. This receptor bound to the beads in a manner consistent with $LR^F G$ formation. In FIG. 4C, background binding of this receptor, with saturating amounts of the non-fluorescent ligand fMLFFGGK, to uncoated beads gave a background binding equivalent to about 5,000 fluors, binding to βγ-coated beads to about 30,000 fluors, and binding to αβγ -coated beads to about 60,000. The assembly on the βγ beads was likely due to the endogenous $α_i$ subunit from the solubilized receptor preparation, since in the presence of GTPγS the signal was virtually the same as background. The control experiment with no receptor in the assembly reaction was not carried out, as the GFP (without receptor) had a hexahistidine tag on it. The control experiment without ligand gave nearly the same signal as the nonspecific binding. The best total binding to background ratio (bar 3 compared to bar 4) was 4.9/1, slightly better than above. Thus, three FPR variants were used to demonstrate the formation of an LRG complex on beads. At least tens of thousands of each of the ternary complexes could be formed on the beads.

Figure 5A:
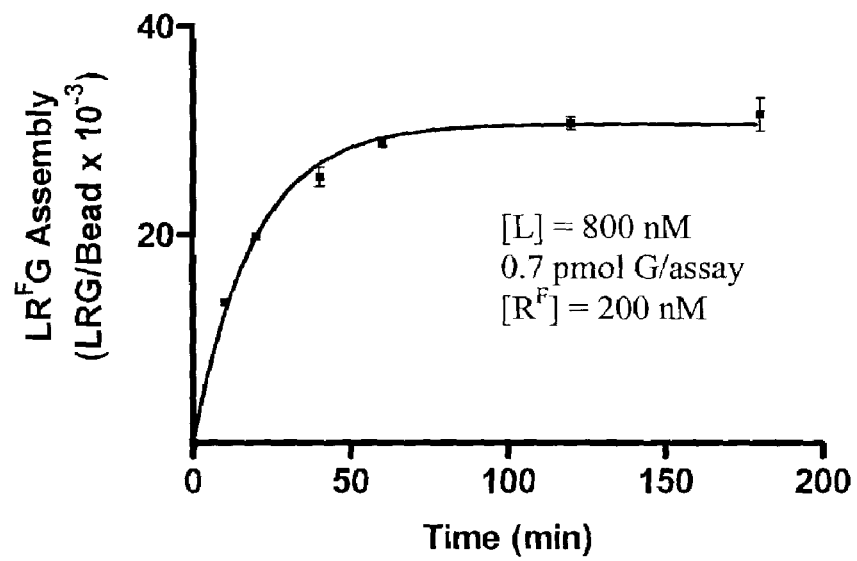
FIGS. 5A, 5B, 5C, 5D and 5E show the effects of time and ternary complex partner concentrations on LRG assembly. The standard assembly for $LR^FG$ (see the experimental procedures contained herein; scheme of FIG. 3, complex D) was used for FIGS. 5A, 5B, 5C and 5D.

Kinetics and Concentration Dependences of the Standard LRG Assembly. The availability of three receptor forms provided a unique opportunity to evaluate the affinity of individual steps of the ternary complex model (L to R, LR to G, and α to βγ). To accomplish this task, the assembly time course for $LR^F G$ assembly was determined (schematic of FIG. 3, complex D), which revealed a halftime of 13 minutes and a calculated association of ~30,000 $LR^F G$ complexes/bead (FIG. 5A). Other experiments showing that maximum assembly was achieved in one to three hours led to the selection of two hours as the standard time of assembly, which is therefore near equilibrium.

Figure 5B:
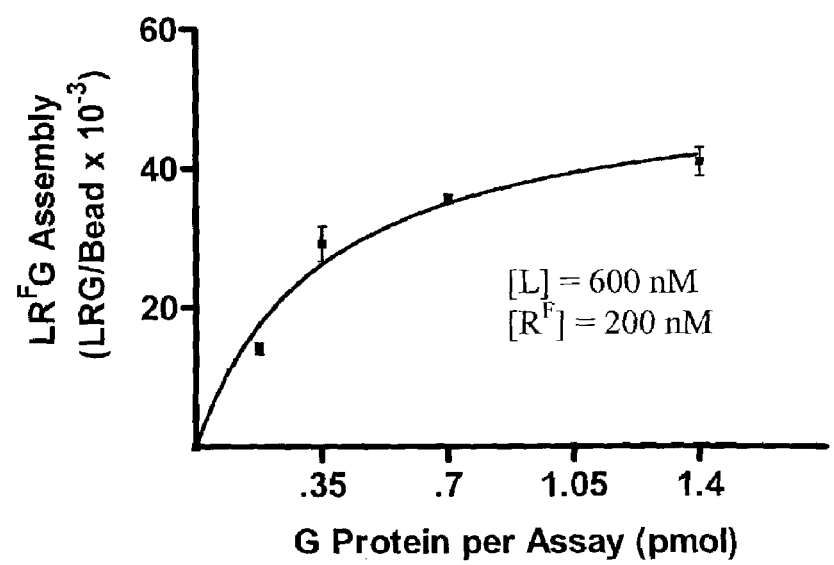

In FIG. 5B, the amount of G protein incubated with the beads in the standard coating procedure was varied; the line shown is a fit to a simple binding curve, giving half saturation of the beads at 0.35 pmol G applied per assembly, corresponding to about 9 million αβγ provided per bead, and a $B_{max}$ of 50,000 $LR^F G$ per bead. This curve reflects bead saturation, rather than an $EC_{50}$ for LRG assembly, which is described in FIG. 6B. The standard protocol thus resulted in 67% saturation of beads with respect to G protein.

Figure 5C:
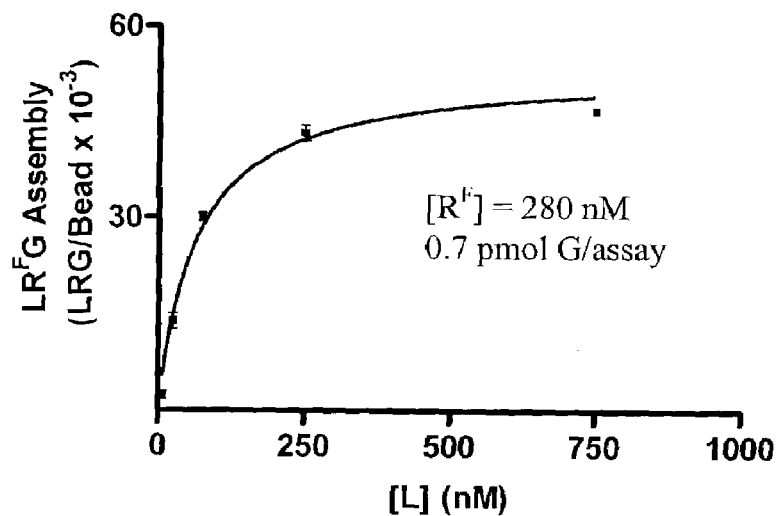

In FIG. 5C, the concentration of L was varied, and the results again followed a simple binding curve, with half-maximal $LR^F G$ assembly at 115 nM L or half of the $R^F$ concentration. Since depletion of $R^F$ was required for the assay, the affinity of L for $R^F$ was not revealed. The standard assembly, with ligand concentration at least 20% higher than the receptor concentration, gave near saturation with respect to LRG assembly.

Figure 5D:
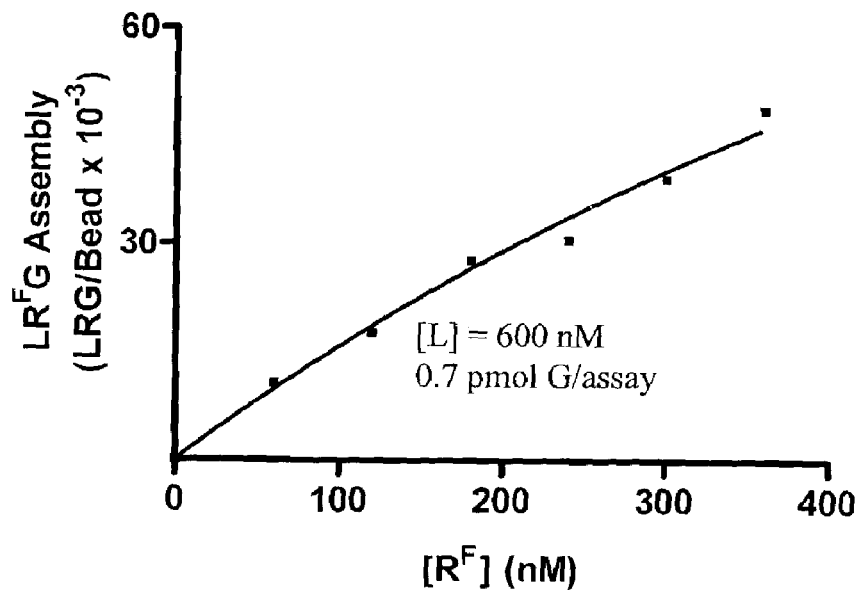

In FIG. 5D, the concentration of $R^F$ was varied with saturating L. The binding was nearly linear over the accessible concentration range of receptor. The fit to the data is for a $K_d$ of 1 μM, consistent with that obtained by solution measurement for LR to G, see Bennett et al. (2001), Real-Time Analysis of G Protein-Coupled Receptor Reconstitution in a Soubilized System, J Biol Chem, 276, pp 22453–22460, the entire contents and disclosure of which is hereby incorporated by reference. The calculated $B_{max}$ was unreliable because the data were obtained at such a low concentration of receptor compared to the dissociation constant. The standard assembly at 200 nM $R^F$ was thus saturating for time and ligand, 67% saturating for G protein, and gave about 30,000 $LR^F G$ ternary complexes per bead.

Figure 5E:
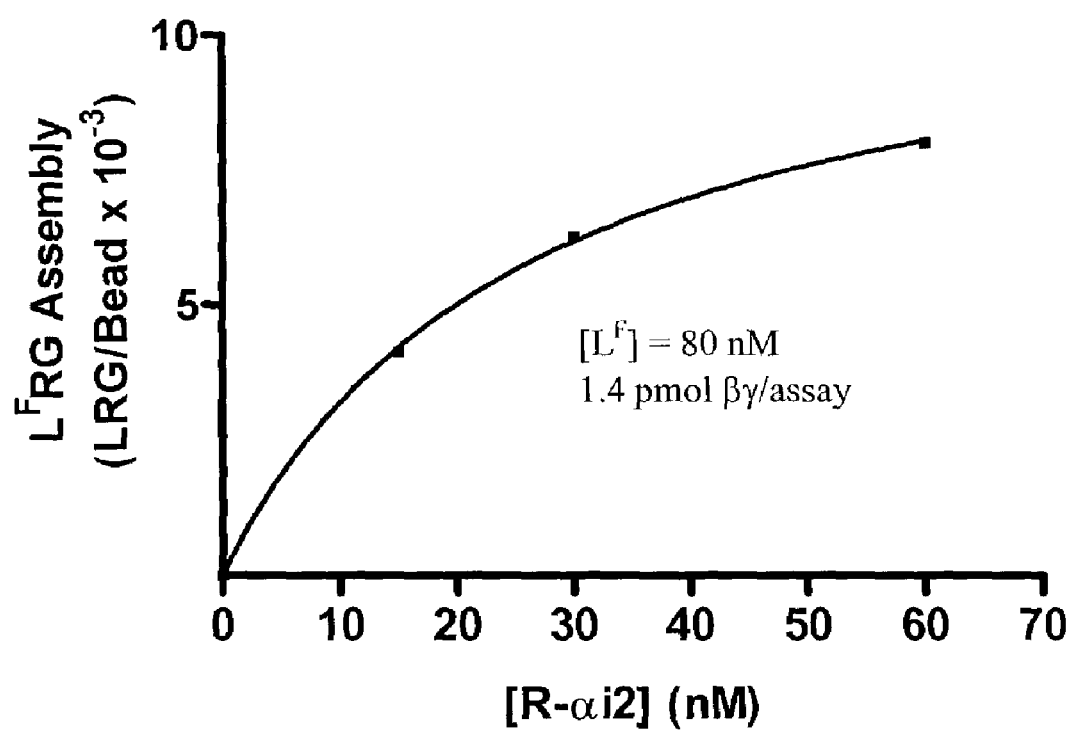

An analogous experiment was performed for the $L^F R$-αGβγ assembly (schematic of FIG. 3, complex C). This examined the affinity of the α to βγ interaction using βγ on the beads, the FPR-Gαi2 fusion protein, and excess fluorescent ligand (FIG. 5E). The apparent $K_d$ of the R-α to βγ assembly was 26 nM, similar to but higher than that observed previously in detergent solutions with fluorescent subunits alone on beads, 3–9 nM, see Sarvazyan et al. (1998), Determinants of Gi1Alpha and Beta Gamma Binding: Measuring High Affinity Interactions in a Lipid Environment Using Flow Cytometry, J Biol Chem, 273, pp 7934–7940, the entire contents and disclosure of which is hereby incorporated by reference. The lower amount of assembly compared to FIGS. 5A, 5B, 5C and 5D is a reflection of assembly in the absence of GTP (as in FIG. 4B, bar 3).

Figure 6B:
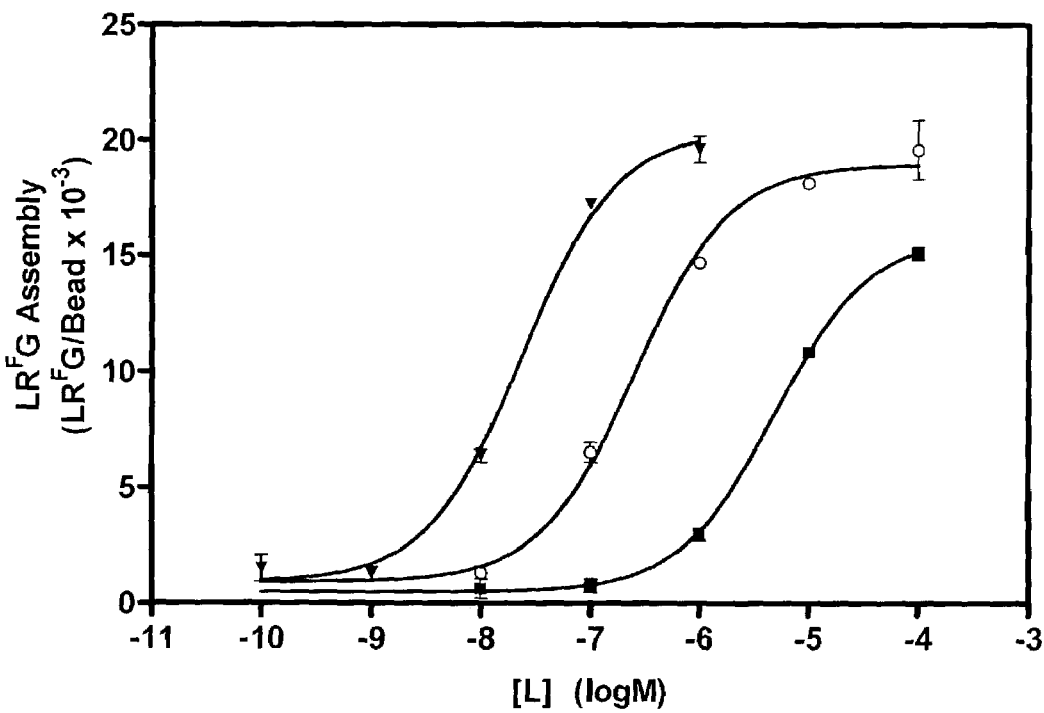

Comparison of LR and LRG Affinities for a Family of Non-fluorescent Ligands. The complexes on particles offered the ability to examine mechanistic features of ternary complex assembly. First, the $K_d$s of a series of unlabelled ligands for the FPR were determined by spectrofluorimetry (FIG. 6A) and compared to LRG assembly (FIG. 6B). Competitive binding experiments were conducted in which increasing amounts of $L^F$ were allowed to compete with a fixed amount of fluorescent ligand and soluble receptor. $IC_{50}$ values were converted to $K_d$ values, using the known concentrations of $L^F$, R, and the $K_d$ of $L^F$ for R. The $K_d$ for fMLFF was $7.5+/-0.8 \times 10^{-8}$ M; for fMLF was $2.3+/-1.6 \times 10^{-6}$ M; and for fML was $1.5+/-0.9 \times 10^{-5}$ M.

The $EC_{50}$ values of the ligands for LRG formation were determined using the standard LRG assembly, as shown in FIG. 6B. Assemblies were conducted in which increasing amounts of each non-fluorescent ligand were added to the standard assembly with 30 nM $R^F$. The $EC_{50}$ value for fMLFF was 2.7+/−0.4×10$^{-8}$ M; for fMLF was 5.5+/−3×10$^{-7}$ M; and for fML was 5.3+/−0.4×10$^{-6}$ M. The ratios of $K_d$ (for LR) to $EC_{50}$ (for LRG formation) for fMLFF was 2.8; for fMLF was 4.2; and for fML was 2.8. These data suggest that LRG assembly is a function of occupancy. The calculated maximal assembly of fML was 78+/−3% of the LRG assembly of the longer peptides. Although obtained near the limit of solubility of fML, the data suggest the possibility of partial agonism at the LRG assembly step in signal transduction, consistent with partial agonism for the dipeptide fMF for oxidant production in cells, see Sklar et al. (1985), Competitive Binding Kinetics in Ligand-Receptor-Competitor Systems: Rate Parameters for Unlabeled Ligands for the Formyl Peptide Receptor, Mol Pharmacol, 28, pp 323–330, the entire contents and disclosure of which is hereby incorporated by reference.

RGS Activity Affects LR-αG Assemblies on Beads. As a second mechanistic problem, the role of GTP and RGS activity in regulating the assembly of βγ subunits with the receptor-Giα fusion protein was examined (FIG. 7; see also FIGS. 3, complex C and FIG. 4B). Because the assembly depended upon the high affinity α to βγ interaction (~10$^{-8}$ M), rather than the lower affinity interaction between R and G in detergent (~10$^{-6}$ M), complexes were formed at near stoichiometric ratios of the components. The data were consistent with the idea that RGS, by enhancing the cleavage of GTP, affected the GTP dose-response for the formation of the bead-based complex. The shift in the dose-response was consistent with the consumption of 10 μM or more GTP in 10 μl over 2 hours in the presence of R-α, RGS, and L. Calculating that 24 nM R-α (the total added) consumed 10 μM GTP equally in the first half hour, leaving 60 minutes for assembly on the bead, the turnover number was ~14 min$^{-1}$ for the receptor-Giα fusion protein at 7° C.; if rates double for every 10° C. increase, this would imply about 110 min$^{-1}$ at 37° C. Calculating consumption over the entire time yields ~5 and 40 min$^{-1}$, respectively.

Real Time Dissociation Kinetics by Flow Cytometry. To assess a third mechanistic potential, ternary complex disassembly with wild type receptor and $L^F$ was examined. LRG complexes generally display a higher affinity for L than do LR complexes alone, see Gilman A G (1987), G Proteins: Transducers of Receptor-Generated Signals, Annu Rev Biochem, 56, pp 615–649, the entire contents and disclosure of which is hereby incorporated by reference, and a slower dissociation rate of ligand from LRG complexes than from LR complexes of FPR in detergent was observed, see Bennett et al. (2001), Real-Time Analysis of G Protein-Coupled Receptor Reconstitution in a Soubilized System, J Biol Chem, 276, pp 22453–22460; Bennett et al. (2001), Partial Phosphorylation of the N-Formyl Peptide Receptor Inhibits G Protein Association Independent of Arrestin Binding, J Biol Chem, 276, pp 49195–49203; and Key et al. (2001), Regulation of Formyl Peptide Receptor Agonist Affinity by Reconstitution with Arrestins and Heterotrimeric G Proteins, J Biol Chem, 276, pp 49204–49212, the entire contents and disclosures of which are hereby incorporated by reference. Ternary complex disassembly was anticipated after GTPγS addition with a halftime <<14 seconds, the halftime associated with LR dissociation in solution (FIG. 2A) and on beads (FIG. 1F; see Table 1 below).

Compilation of equilibrium and kinetic dissociation data for $L^F R$ complexes and of kinetic dissociation data for $L^F RG$ complexes of the formyl peptide receptor. In all cases, $L^F R$ equilibria and disassembly rates were not sensitive to GTPγS addition, whereas $L^F RG$ assembly and $L^F RG$ dissociation rates were sensitive to GTPγS addition at 10$^4$ M. $L^F RG$ data were obtained with wild type FPR. Notes: (a) wild-type FPR, (b) N-H6:FPR, (c) FPR:C-H6, (d) αi3 and bovine brain βγ, see Bennett et al. (2001), Real-Time Analysis of G Protein-Coupled Receptor Reconstitution in a Solubilized System, J Biol Chem, 276, pp 22453–22460, the entire contents and disclosure of which is hereby incorporated by reference, (e) αi3β1γ2, (f) αi3β4γ2. Values of $K_d$ showed a variance of thirty percent, and values of $t_{1/2}$ showed a variance of ten percent, unless otherwise noted.

TABLE 1

|  | $L^F R$ | | $L^F RG\ t_{1/2}$ (sec) | |
| --- | --- | --- | --- | --- |
|  | $K_d$ (nM) | $t_{1/2}$ (sec) | (−) GTPγS | (+) GTPγS |
| Soluble | 5[a] | 14[a] | 80–120[d] | 20–22[d] |
|  | 7[b] | 15[b] |  |  |
|  | 10[c] | 14[c] |  |  |
| Bead-based | 8[b] |  | >100[e] | <5 |
|  | 4[c] | 14[c] | >100[f] | 5–10 |

Figure 8A:
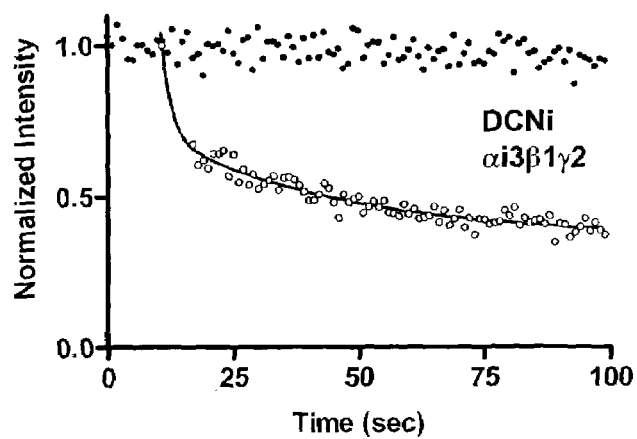
FIGS. 8A, 8B and 8C show LRG disassembly with GTPγS.
Figure 8B:
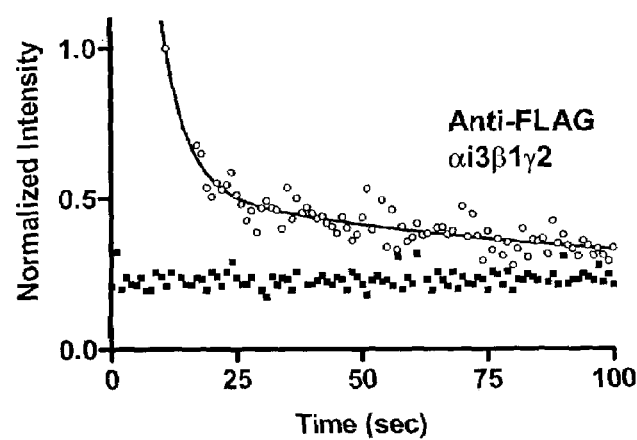
Figure 8C:
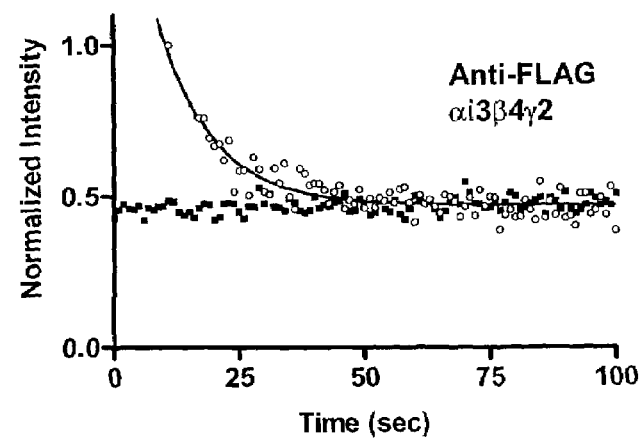
Figure 9A:
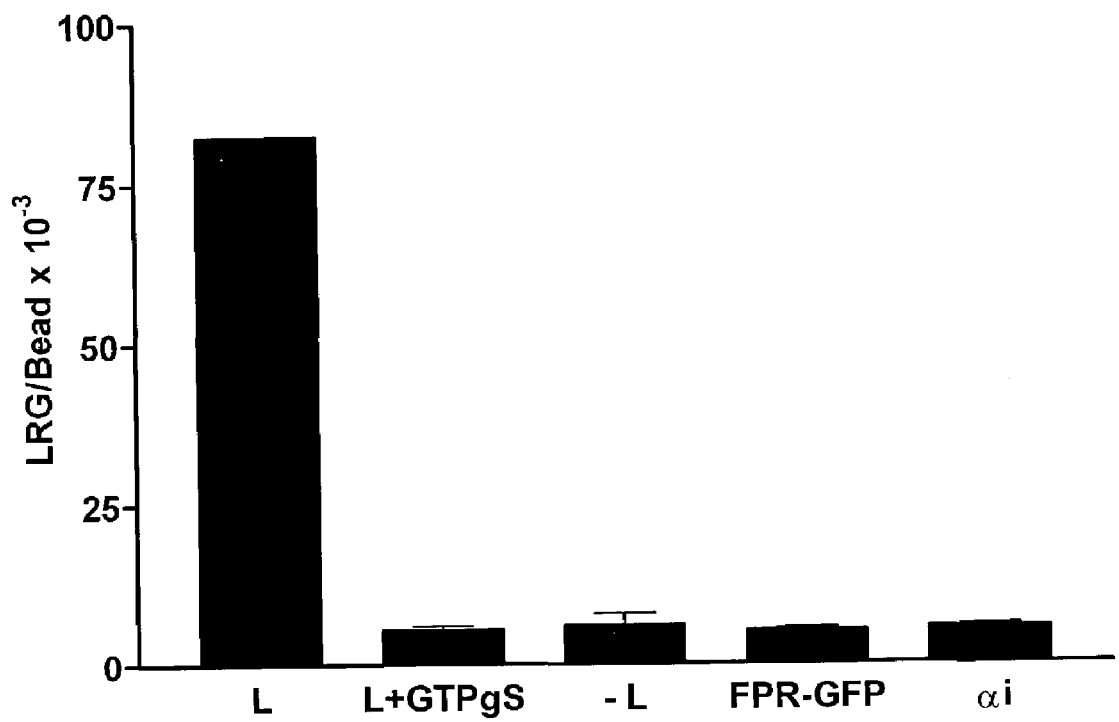
FIGS. 9A, 9B, 9C and 9D show characterization of an LRG assembly assay.
Figure 9B:
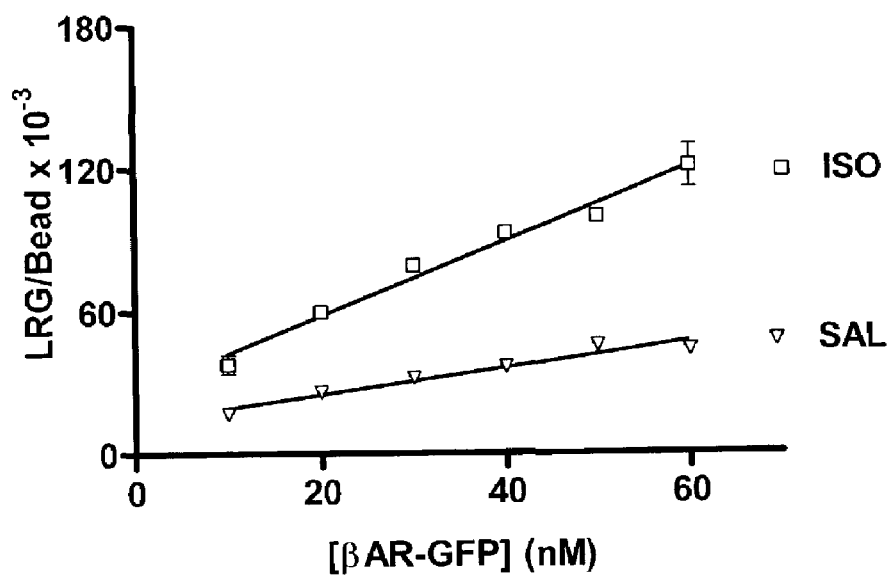
Figure 9C:
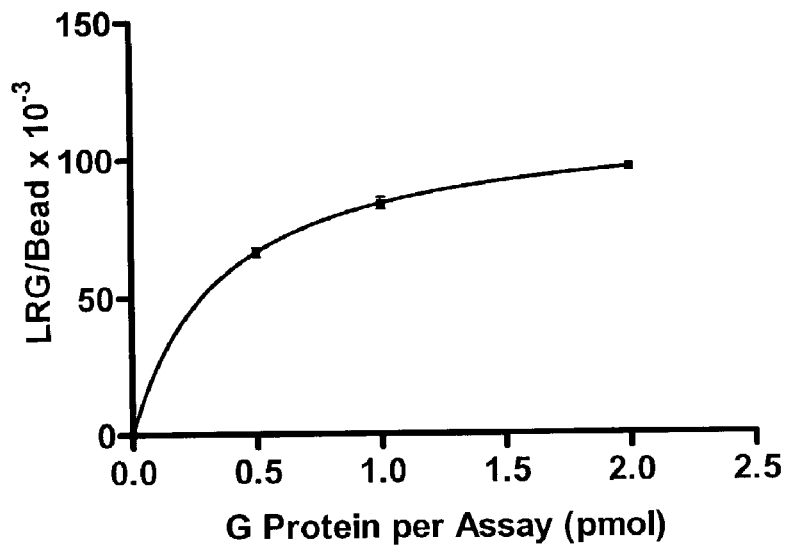
Figure 9D:
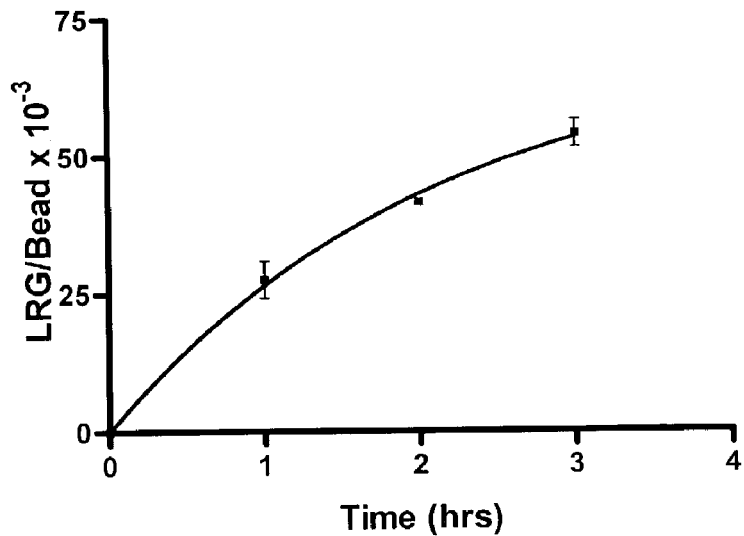

The dissociation of LRG complexes was followed by flow cytometry using manual addition of GTPγS to the bead suspensions (FIG. 8). FIG. 8A shows results using $L^F RG$ on DCNi beads. The halftime for loss of fluorescence ($L^F$) from the particles in the absence of nucleotide was much greater than 100 seconds, corresponding to $L^F RG$. At saturating GTPγS a fast component was observed, with a halftime of <5 seconds, or faster than LR dissociation. To evaluate the possibility that non-specific interactions were contributing to the stability on the DCNi beads, complexes using streptavidin beads were assembled, coated with a biotin labeled anti-FLAG antibody, then coated with αi3+βγ-FLAG complexes as described in the experimental procedures discussed herein. Studies were performed with two different β subunits, β1 and β4, which have both been shown to complex efficiently with receptors in αi1 complexes, see Lim et al. (2001), Receptor-G Protein Gamma Specificity: Gamma11 Shows Unique Potency for A(1) Adenosine and 5-HT(1A) Receptors, Biochemistry, 40, pp 10532–10541, the entire contents and disclosure of which is hereby incorporated by reference. In assemblies here with αi3 and $L^F$, guanine nucleotide was able to induce dissociation when using β1γ2, in which a fast component was observed, again with a halftime of <5 seconds, and a second, slower component with a halftime of 10–40 seconds (FIG. 8B, and Table 1). Using β4γ2, a single exponential decay was observed, with a halftime of <10 seconds (FIG. 8C). As in earlier studies using different α subunits, see Bennett et al. (2001), Real-Time Analysis of G Protein-Coupled Receptor Reconstitution in a Solubilized System, J Biol Chem, 276, pp 22453–22460, the entire contents and disclosure of which is hereby incorporated by reference, the reconstitution of the formyl peptide receptor into a ternary complex was more efficient with αi3 than αi2 (not shown).

Discussion

The present invention demonstrates the formation of LRG complexes on beads with three FPR variants. It extends work in which reconstitution of soluble receptors with signal transduction partners has been a valuable adjunct to cell physiology and confocal microscopy, see Bennett et al. (2001), Partial Phosphorylation of the N-Formyl Peptide Receptor Inhibits G Protein Association Independent of Arrestin Binding, J Biol Chem, 276, pp 49195–49203, the entire contents and disclosure of which is hereby incorporated by reference. Achieving ternary complex formation in detergent on particles involved evaluating several types of beads, attachment schemes with several epitope tags, and several approaches to tether ternary complexes. These included using hexahistidine-tagged receptors on DCNi beads (FIG. 2E) and biotinylated ligand on streptavidin beads (not shown). With hexahistidine-tagged receptors, the problem was nonspecific binding of G proteins to the particles. The biotinylated ligands that recognized soluble receptors in suspension did not capture those receptors on beads.

Assembly and Detection of Ternary Complexes on Beads. The wild type receptor (R) used in the $L^FRG$ assembly provides a direct comparison to the assembly of $L^FRG$ in solution, see Bennett et al. (2001), Real-Time Analysis of G Protein-Coupled Receptor Reconstitution in a Soubilized System, J Biol Chem, 276, pp 22453–22460; Bennett et al. (2001), Partial Phosphorylation of the N-Formyl Peptide Receptor Inhibits G Protein Association Independent of Arrestin Binding, J Biol Chem, 276, pp 49195–49203; and Key et al. (2001), Regulation of Formyl Peptide Receptor Agonist Affinity by Reconstitution with Arrestins and Heterotrimeric G Proteins, J Biol Chem, 276, pp 49204–49212, the entire contents and disclosures of which are hereby incorporated by reference. The conditions (60 nM R, 75 nM $L^F$, $K_d$=5 nM) ensured nearly quantitative conversion of R to $L^FR$, with 15 nM $L^F$ free to interact with the beads nonspecifically. The unavailability of fluorescent ligands for other GPCRs is a barrier to transferring this technology. While the receptor-Gαi2 (R-αi2) construct allows high affinity complex assembly with the α subunit available at no additional cost, it still uses a fluorescent ligand for detection and is not applicable to other receptors. The receptor-GFP fusion protein ($R^F$) allows quantification of the receptor, and obviates the development of a fluoresceinated ligand for every GPCR. It is a valuable construct for high throughput drug discovery applications. A triple fusion protein incorporating receptor, Gα subunit, and GFP, see Bevan et al. (1999), Functional Analysis of a Human A(1) Adenosine Receptor/Green Fluorescent Protein/G(I1)Alpha Fusion Protein Following Stable Expression in CHO Cells, FEBS Lett, 462, pp 61–65, the entire contents and disclosure of which is hereby incorporated by reference, would allow high affinity assemblies to be generalized to other receptors.

Affinities of the Components of the Complexes. Previous work with the solubilized FPR, see Bennett et al. (2001), Real-Time Analysis of G Protein-Coupled Receptor Reconstitution in a Soubilized System, J Biol Chem, 276, pp 22453–22460; Bennett et al. (2001), Partial Phosphorylation of the N-Formyl Peptide Receptor Inhibits G Protein Association Independent of Arrestin Binding, J Biol Chem, 276, pp 49195–49203; Key et al. (2001), Regulation of Formyl Peptide Receptor Agonist Affinity by Reconstitution with Arrestins and Heterotrimeric G Proteins, J Biol Chem, 276, pp 49204–49212; and Sklar et al. (2000), Solubilization and Display of G Protein-Coupled Receptors on Beads for Real-Time Fluorescence and Flow Cytometric Analysis, Biotechniques, 28, pp 975–976, the entire contents and disclosures of which are hereby incorporated by reference, enabled an analysis of the affinities of LR and LRG. The assembly of LRG in detergent solution took place in a 10 µl volume, with high concentrations of all components, as did assembly onto G protein coated beads. The two-hour time for assembly in solution was similar to assembly on the bead. Because of the high receptor concentration, ligand depletion at concentrations of ligand similar to that of receptor prevented direct analysis of L affinity with the $LR^FG$ complex. Because the receptor concentration was <500 nM, it was difficult to unequivocally determine the affinity of $LR^F$ for G, but the data were consistent with $K_d$ ~1 µM, similar to the solution value, see Bennett et al. (2001), Real-Time Analysis of G Protein-Coupled Receptor Reconstitution in a Soubilized System, J Biol Chem, 276, pp 22453–22460; Bennett et al. (2001), Partial Phosphorylation of the N-Formyl Peptide Receptor Inhibits G Protein Association Independent of Arrestin Binding, J Biol Chem, 276, pp 49195–49203; and Key et al. (2001), Regulation of Formyl Peptide Receptor Agonist Affinity by Reconstitution with Arrestins and Heterotrimeric G Proteins, J Biol Chem, 276, pp 49204–49212, the entire contents and disclosures of which are hereby incorporated by reference. The α to βγ affinity in the presence of LR, 26 nM, was based on the binding of R-αi2 to βγ. This is similar to the affinity observed in detergent with fluorescent subunits alone on beads, 3–9 nM, see Sarvazyan et al. (1998), Determinants of Gilalpha and Beta Gamma Binding: Measuring High Affinity Interactions in a Lipid Environment Using Flow Cytometry, J Biol Chem, 273, pp 7934–7940, the entire contents and disclosure of which is hereby incorporated by reference.

Applications. The three forms of receptor discussed in the present application allowed assemblies to be probed in novel ways. FPR-GFP was used to study ternary complexes for a family of ligands, the FPR-αi2 for RGS activity, and the wild type receptor for ternary complex disassembly kinetics. For a set of agonists, the affinities of LR and LRG varied essentially in parallel over three orders of magnitude with a hint that a partial agonist might be reflected in suboptimal assembly (FIG. 6). Similar results have been observed for the β2-adrenergic receptor (data not shown) with the efficacy of partial agonists reflected in suboptimal LRG assembly. Antagonists, and full and partial agonists have been simultaneously discriminated among in a format compatible with high throughput (see Marcus Evans Conference 'High Throughput Screening for Drug Discovery', Boston, Mass.; www.melifesciences.com; Simons PC, et al.).

The nucleotide sensitivity of the assembly of R-αi2 with βγ allowed the activity and specificity of RGS to be examined. While RGS4, RGS7 (not shown) and RGS8 appeared to consume GTP in the presence of LR-α, RGS2 did not, as expected, see Lan et al. (2000), Rapid Kinetics of Regulator of G-Protein Signaling (RGS)-Mediated Galphai and Galphao Deactivation: Galpha Specificity of RGS4 and RGS7, J Biol Chem, 275, pp 33497–33503, the entire contents and disclosure of which is hereby incorporated by reference. This assembly format therefore has the potential for discriminating RGS antagonists. Elsewhere it is described how GTP increases access of soluble assemblies of R-αi2 to anti-αi2 antibody, consistent with the idea of Aγ binding and release (Shi M, et al., submitted).

The assembly and disassembly kinetics of complexes on particles may provide insight into the ternary complex activation. FIGS. 1 and 2 show dissociation of $L^FR$ and $L^FC$-H6:FPR on DCNi beads (halftime ~14 sec in solution and on beads). The dissociation of $L^FR\alpha\beta\gamma$ on beads was far slower, but enhanced by the binding of GTPγS to a halftime faster than that observed for LR (FIG. 8). The combination of sensitivity of LRG and insensitivity of LR to nucleotide, the $K_d$s, and the kinetics, summarized in Table 1, indicates that both binary and ternary complexes on beads as well as in solution may be observed.

The wild type ternary complex ($L^FR\alpha\beta\gamma$) dissociation was characterized in FIG. 8. During cell activation, the dissociation of R from α, or of α from βγ, could occur on a time frame much faster than LR dissociation. Either of these mechanisms would account for loss of fluorescence from the bead at a rate greater than dissociation of $L^F$ from R. Because non-specific interactions between proteins and DCNi beads could stabilize assembly and slow disassembly, the measurements were repeated with streptavidin beads, biotinylated anti-FLAG antibody, and FLAG-tagged βγ dimer. In all cases (two types of beads, two β, subunits), there was a fast component of dissociation that appeared, as expected, to be faster than dissociation of $L^F$ from R. These results are consistent with activation faster than ligand release, and indicate the potential of bead assemblies for mechanistic analysis. We previously showed that nucleotide binding induced a shift in affinity consistent with a millisecond conversion from LRG to LR in membranes, Neubig R R and Sklar L A (1993), Subsecond Modulation of Formyl Peptide-Linked Guanine Nucleotide-Binding Proteins by Guanosine 5'-O-(3-Thio)Triphosphate in Permeabilized Neutrophils, Mol Pharmacol, 43, pp 734–740, the entire contents and disclosure of which is hereby incorporated by reference, and observed a fast conversion in detergent, see Bennett et al. (2001), Real-Time Analysis of G Protein-Coupled Receptor Reconstitution in a Solubilized System, J Biol Chem, 276, pp 22453–22460, the entire contents and disclosure of which is hereby incorporated by reference. These analyses did not allow us to identify the species responsible for LR-like behavior (i.e., LR, LRG-GTP, LRα-GTP, etc.). With the appropriate time resolution, the three different types of receptor assemblies should reveal the precise species present. A stopped-flow flow cytometer with resolution to ~40 msecs, see Graves et al. (2002), Nozzle Design Parameters and Their Effects on Rapid Sample Delivery in Flow Cytometry, Cytometry, 47, pp 127–137, the entire contents and disclosure of which is hereby incorporated by reference, and stopped-flow injection without sheath flow control, see Seamer et al. (1999), Sheath Fluid Control to Permit Stable Flow in Rapid Mix Flow Cytometry, Cytometry, 35, pp 75–79, the entire contents and disclosure of which is hereby incorporated by reference, provide the potential for 200 millisecond resolution (FIG. 2D). A triple fusion protein (R-α-GFP) should distinguish ligand disassembly from αβγ disassembly and activation, see Bevan et al. (1999), Functional Analysis of a Human A(1) Adenosine Receptor/Green Fluorescent Protein/G(11) Alpha Fusion Protein Following Stable Expression in CHO Cells, FEBS Lett, 462, pp 61–65, the entire contents and disclosure of which is hereby incorporated by reference.

Beads. The bead display of LRG complexes appears to be general. LRG formation occurs for three forms of FPR (wild type, receptor-Gα, and receptor-GFP), two epitope tags (hexahistidine and FLAG), two Gα subunits (αi2, (αi3) and two Gβ subunits (β1 and β4). Ternary complex formation has also been demonstrated with a β2-adrenergic receptor-GFP fusion protein (see FIGS. 9A, 9B, 9C and 9D). Other types of molecular assemblies are amenable to this technology.

Non-specific binding with nickel-chelate beads is a potential problem. For purified hexahistidine-tagged GFP, total binding was several million sites per bead. ~80% could be blocked by bovine serum albumin. ~400,000 epitope-tagged receptors from a crude mixture of sublilized proteins bound particle. For optimal ternary complex formation, ~100,000 G protein sites per particle were accessible. It may be that the purified H6-GFP binding (FIG. 2) reflects all possible modes of binding (hexahistidine-tag dependent and independent), and is within an order of magnitude or less of covering the surface. On the other hand, specific binding of the non-his-tagged receptor plus ligand to G beads represent G proteins that are displayed in correct orientation on the surface, ~100,000. Most of the G protein, between the 100,000 displayed correctly and the total number of binding sites (>3 million), should be bound non-specifically and with improper orientation. The use of anti-FLAG beads avoids this problem, see Buranda et al. (2001), Detection of Epitope-Tagged Proteins in Flow Cytometry: Fluorescence Resonance Energy Transfer-Based Assays on Beads with Femtomole Resolution, Anal Biochem, 298, pp 151–162, the entire contents and disclosure of which is hereby incorporated by reference.

Screening and proteomics. The receptor-GFP fusion protein should adapt to high throughput screening, especially when coupled to HyperCyt™ which delivers beads to a flow cytometer from multiwell plates, see Kuckuck et al. (2001), High Throughput Flow Cytometry, Cytometry, 44, pp 83–90 and Jackson et al. (2002), Mixing Small Volumes for Continuous High-Throughput Flow Cytometry: Performance of a Mixing Y and Peristaltic Sample Delivery, Cytometry, 47, pp 183–191, the entire contents and disclosures of which are hereby incorporated by reference. Particle based screening is compatible with a search for ligands for both known and orphan receptors, see Stadel et al. (1997), Orphan G Protein-Coupled Receptors: a Neglected Opportunity for Pioneer Drug Discovery, Trends Pharmacol Sci, 18, pp 430–437, the entire contents and disclosure of which is hereby incorporated by reference, agonists promoting assembly on particles, and antagonists inhibiting them. Proteomics applications could be based on bead arrays, see Nolan J P and Sklar L A (1998), The Emergence of Flow Cytometry for Sensitive, Real-Time Measurements of Molecular Interactions, Nat Biotechnol, 16, pp 633–638, the entire contents and disclosure of which is hereby incorporated by reference, in this situation, color-coded particles would display individual αβγ combinations, one combination per color code. Specific subunit interactions could be assessed as a GFP-receptor binds to a subset of the combinations. Commercial hardware and software are already available for decoding the results of soluble, multiplex cytometric arrays, see Lund-Johansen et al. (2000), Flow Cytometric Analysis of Immunoprecipitates: High-Throughput Analysis of Protein Phosphorylation an Protein-Protein Interactions, Cytometry, 39, pp 250–259, the entire contents and disclosure of which is hereby incorporated by reference. Our standard coating of the nickel beads uses 0.7 pmol of Gαβγ per assay to obtain a 3 to 1 ratio of total signal to nonspecific signal, while the anti-FLAG beads use 0.17 pmol of Gαβγ per assay to obtain the same 3 to 1 ratio, using tens of thousands of beads. Smaller volumes and fewer beads would produce a more efficient screening process.

The present invention employs a flow cytometry device to perform measurements of the formation of complexes in a moving liquid stream. In the flow cytometry device a liquid stream forming a sheath fluid into which a sample is introduced is focused through an orifice. As the objects pass through the orifice, particular characteristics of the objects are determined based upon the analyzing or counting capabilities of the flow cytometry device. Typically, the flow cytometry device of the present invention is capable of sorting or counting at high speeds, collecting tens of thousands of objects.

Although many conventional flow cytometry devices may be used in the method of the present invention, one preferred commercially available flow cytometer is the FACScan™ instrument sold by Becton Dickinson Immunocytometry Systems, San Jose, Calif., which relies on a hydrodynamically focused fluid system. The FACScan™ instrument rapidly analyzes cells on the basis of fluorescence and light scatter properties. Analysis is accomplished by introducing cells in a suspension to the center of a focused liquid stream thus causing them to pass, one at a time, through a focused light from a high powered laser. Each cell is individually characterized by its light scatter signals and by the intensity and color of fluorescence emitted while it is illuminated. This system is described in U.S. Pat. No. 4,844,610 issued Jul. 4, 1989 to North, U.S. Pat. No. 5,030,022 issued Jul. 9, 1991 to North and U.S. Pat. No. 5,040,890 issued Aug. 20, 1991 to North, the entire contents and disclosures of which are hereby incorporated by reference.

All documents, patents, journal articles and other materials cited in the present application are hereby incorporated by reference.

Although the present invention has been fully described in conjunction with the preferred embodiment thereof with reference to the accompanying drawings, it is to be understood that various changes and modifications may be apparent to those skilled in the art. Such changes and modifications are to be understood as included within the scope of the present invention as defined by the appended claims, unless they depart therefrom.

What is claimed is:

1. A method for detecting ligand-receptor-GPCR complexes, comprising the steps of:
   (a) providing a sample suspension containing at least one set of G-protein beads, wherein said G-protein beads are epitope-recognizing beads having an epitope-containing heterotrimeric G-protein bound thereto;
   (b) mixing said sample suspension with at least one type of G-protein coupled receptor and a ligand wherein said receptor or said ligand contains a detectable label, to thereby form a mixed suspension containing a detectable ligand-receptor-G protein complex when said G protein forms said detectable complex with said receptor and said ligand;
   (c) detecting said ligand-receptor-G protein complexes in said mixed suspension by flow cytometry.

2. The method of claim 1, wherein said receptor and said ligand are known to form a complex with another G-protein.

3. The method of claim 1, wherein said G protein and said receptor are known to form a complex with a second ligand.

4. The method of claim 1, wherein said epitope-recognizing beads are beads that recognize the FLAG epitope.

5. The method of claim 1, wherein said epitope-recognizing beads are beads that recognize the six-histidine (H6) epitope.

6. The method of claim 1, wherein the G-protein coupled receptor is a solubilized receptor.

7. The method of claim 1, wherein said epitope-recognizing beads are derivatized to carry chelated nickel.

8. The method of claim 1, wherein said ligand contains said detectable label and said detectable label is a fluorescent tag.

9. The method of claim 1, wherein said receptor contains said detectable label and said detectable label is a fluorescent tag.

10. The method of claim 9, wherein said receptor is made fluorescent by chemical derivatization of said receptor.

11. The method of claim 9, wherein said receptor is made fluorescent by making a fusion protein of said receptor with a fluorescent protein.

* * * * *